(12) United States Patent
Anderson et al.

(10) Patent No.: US 6,858,393 B1
(45) Date of Patent: Feb. 22, 2005

(54) CHAIN TERMINATORS FOR DNA SYNTHESIS

(75) Inventors: Jack Dewayne Anderson, Oceanside, CA (US); Jeffrey Carl Braman, Carlsbad, CA (US)

(73) Assignee: Stratagene California, La Jolla, CA (US)

( * ) Notice: Subject to any disclaimer, the term of this patent is extended or adjusted under 35 U.S.C. 154(b) by 0 days.

(21) Appl. No.: 10/098,019

(22) Filed: Mar. 13, 2002

(51) Int. Cl.$^7$ .............................. C12Q 1/68; C07F 9/02
(52) U.S. Cl. ......................... 435/6; 435/91.2; 544/243; 544/264
(58) Field of Search .................... 435/6, 91.2; 544/243, 544/264

(56) References Cited

U.S. PATENT DOCUMENTS

| | | | |
|---|---|---|---|
| 5,744,600 A | | 4/1998 | Mansuri et al. ............. 544/243 |
| 6,706,879 B2 | * | 3/2004 | Anderson et al. ............. 546/88 |
| 2003/0088109 A1 | * | 5/2003 | Braman et al. ............. 524/589 |

FOREIGN PATENT DOCUMENTS

| | | | |
|---|---|---|---|
| WO | WO 96/11937 A1 | * | 4/1996 |
| WO | WO 02/68537 A2 | * | 9/2002 |

OTHER PUBLICATIONS

Holy et al. (I), "Synthesis of Isomeric and Enantiomeric O–Phosphonylmethyl Derivatives of 9–(2,3–Dihydroxypropyl)adenine," *Coll. Czech. Chem. Comm.*, 52(11), 2775–2791 (Nov., 1987).*

Holy et al. (II), "Synthesis of Potential Prodrugs and Metabolites of 9–(S)–(3–hydroxy–2–phosphonylmethoxypropyl)adenine," *Coll. Czech. Chem. Comm.*, 52(11), 2792–2800 (Nov., 1987).*

Holy et al. (III), "Synthesis of 9–(S)–(2–phosphonylmethoxyethyl) adenine," *Coll. Czech. Chem. Comm.*, 52(11), 2801–2809 (Nov., 1987).*

Moffatt, J. G., "A General Synthesis of Nucleoside–5' Triphosphates," *Canadian Journal of Chemistry*, 42, 599–604 (1964).*

Starret et al., "Synthesis, Oral Bioavailability Determination, and In Vitro Evaluation of Prodrugs of the Antiviral Agent 9–[2–(Phosphonomethoxy)ethyl] adenine (PMEA)," *Journal of Medicinal Chemistry*, 37(12), 1857–1864 (Jun. 10, 1994).*

Wormstädt et al., "Synthesis of Acylic Nucleoside Phosphonates as Antiviral Compounds," *Journal of Heterocyclic Chemistry*,37, 1187–1191 (Sep. –Oct., 2000).*

Holy et al. (IV). "Structure–Antiviral Activity Relationship in the Series of Pyrimidine and Purine N–[2–(2–Phosphonomethoxy)ethyl]Nucleotide Analogues. 1. Derivatives Substituted at the Carbon Atoms of the Base ," *Journal of Medicinal Chemistry*, 42(12), 2064–2086 (Jun. 17, 1999).*

Holy et al. (V), "Synthesis of N–(2–Phosphonylmethoxyethyl) Derivatives of Heterocyclic Bases," *Coll. Czech. Chem. Comm.*, 54(8), 2190–2210 (Aug., 1989).*

Merta, et al. "Phosphorylation of acyclic nucleotide analogs HPMPA and PMEA in L1210 mouse lukemia cell extracts", Neoplasma, 1990, V.37, pp. 111–120.

Martinez, et al. "Acyclic Nucleoside Triphoshate Analogs as Terminators in Biocatalytic DNA Replication", Bioorganic & Medicinal Chemistry Letters, 1997, vol. 7, No. 23, pp. 3013–3016.

Holy, et al. "Acyclic nucleotide analgues: synthesis, antiviral activity and inhibitory effects on some cellular and virus–encoded enzymes in vitro", Antiviral Research, 13 (1990), pp. 295–311. (Oct. 1, 1989).

Martinez, et al. "An allylic/acyclix adenosine nucleoside triphosphate for termination of DNA synthesis by DNA template–dependent polymerases" Nucleic Acid Research, 1999, vol. 27, No. 5, pp. 1271–1274.

* cited by examiner

*Primary Examiner*—L. E. Crane
(74) *Attorney, Agent, or Firm*—Kathleen M. Williams; Palmer & Dodge LLP

(57) ABSTRACT

The invention relates to acyclic chain terminator nucleotide analogs. More particularly, the invention relates to phosphonomethoxyethyl nucleotide analogs and detectably labeled versions thereof, especially fluorescently labeled versions thereof. The invention further relates to the use of chain terminating phosphonomethoxyethyl nucleotide analogs in methods of synthesizing a polynucleotide, labeling a polynucleotide, determining polynucleotide sequence information, and kits therefor.

37 Claims, 30 Drawing Sheets

| FIG. 2A |
| FIG. 2B |
| FIG. 2C |
| FIG. 2D |

C-5-alkynyl-Fluor-PME-T

N4-Fluor-PME-C

Pyrrazolo[3,4-d]pyrimidine

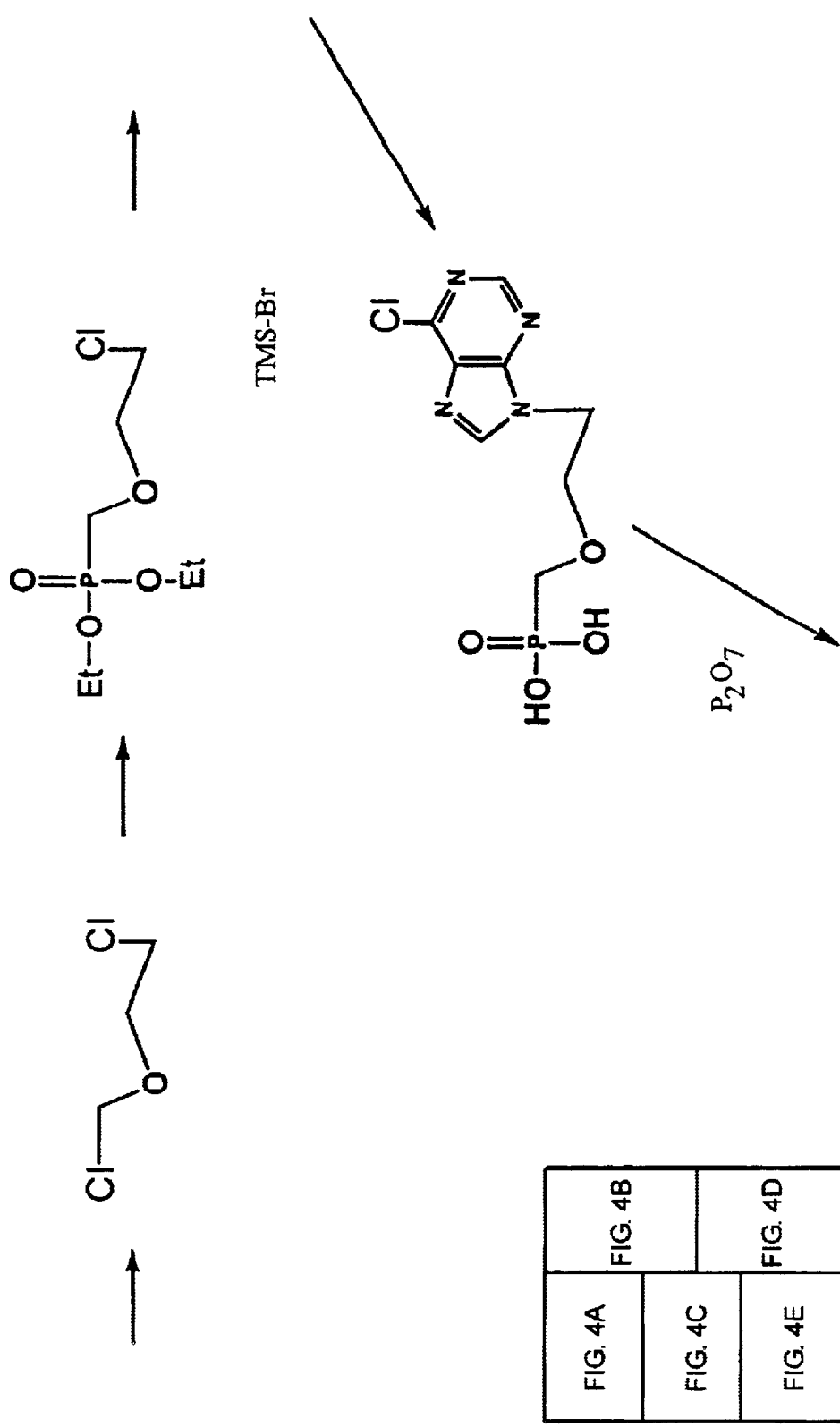

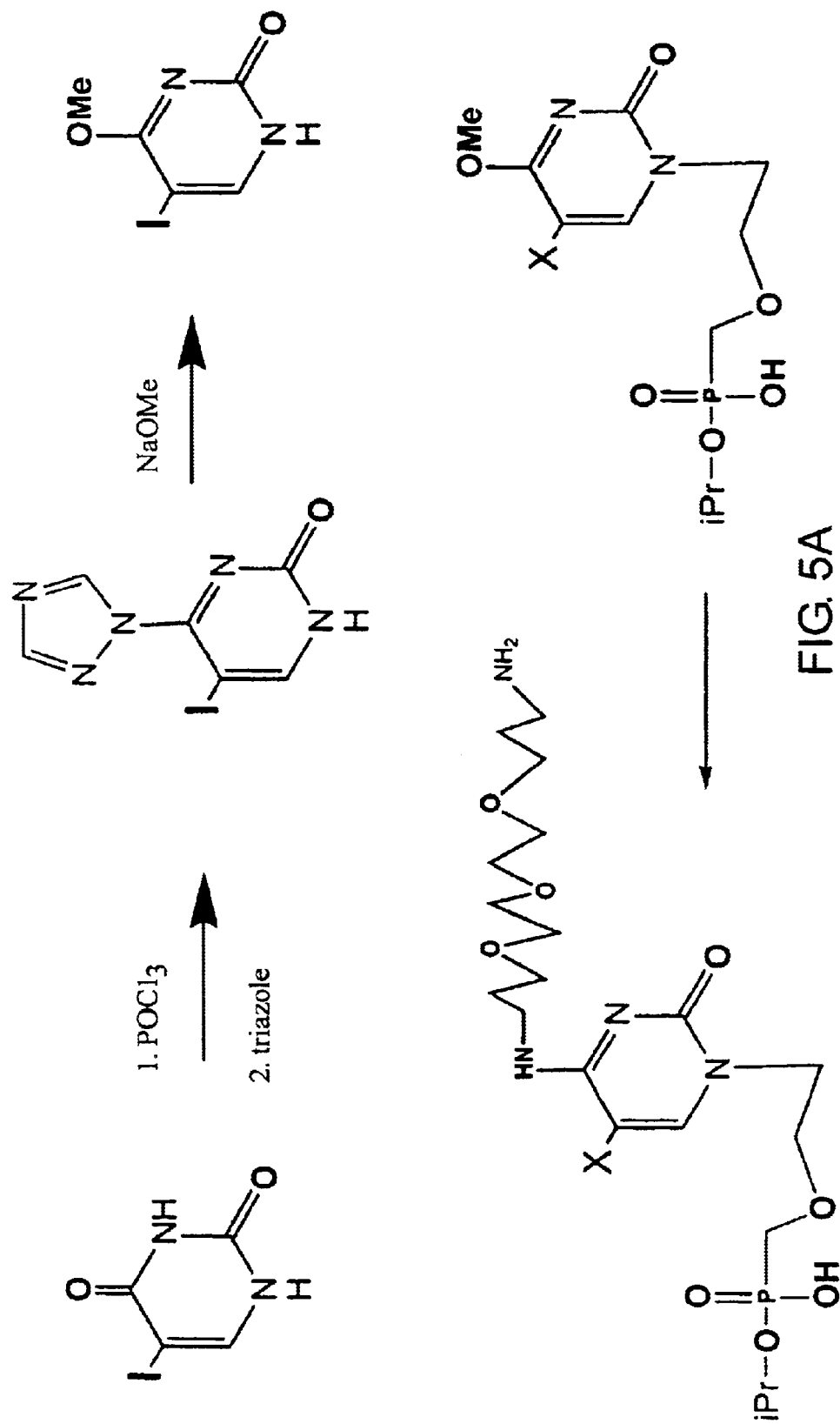

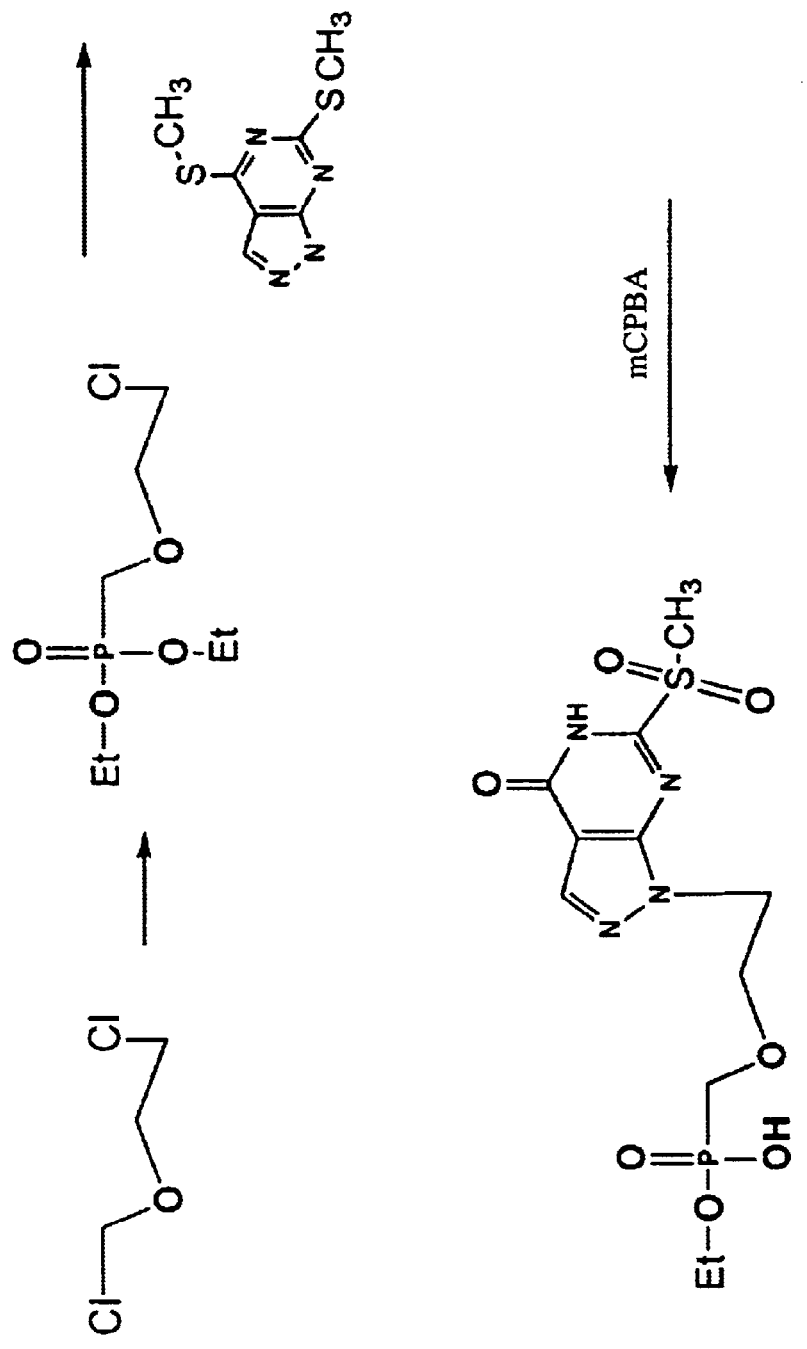
FIG. 7A Synthesis of a Fluorescently Labeled PME-G Analog (6-aminopyrazolo[3,4-d]pyrimidin-4-one)

ddA/dN    PMEA/dN

1/50,1/10,1/5,1/1,5/1,10/1

SEQUENCE LISTING

<160> NUMBER OF SEQ ID NOS: 2

<210> SEQ ID NO 1
<211> LENGTH: 10
<212> TYPE: PRT
<213> ORGANISM: Homo sapiens

<400> SEQUENCE: 1

Glu Gln Lys Leu Ile Ser Glu Glu Asp Leu
1               5                   10

<210> SEQ ID NO 2
<211> LENGTH: 8
<212> TYPE: PRT
<213> ORGANISM: Bacteriophage T7

<400> SEQUENCE: 2

Asp Tyr Lys Asp Asp Asp Asp Lys
1               5

CHAIN TERMINATORS FOR DNA SYNTHESIS

BACKGROUND OF THE INVENTION

With the advent of the Human Genome Project and the field of pharmacogenomics, which aims to correlate sequence polymorphisms with variations in drug responses and disease susceptibility, a heightened need for improved nucleic acid sequencing methods has become apparent.

The most commonly used sequencing methods are variants on the "Sanger" or "dideoxy" method, in which the enzymatic, template dependent incorporation of a chain-terminating dideoxynucleotide results in the generation of a collection of nucleic acid fragments each ending with the base carried by that analog. When a set of four such reactions is performed, one for each of the bases G, A, T and C, the electrophoretically-separated fragments will form a "ladder" from which the sequence can be read.

The efforts to map genomic sequence polymorphisms and mutations, particularly single nucleotide polymorphisms ("SNPs"), have spawned new sequencing technologies aimed at obtaining small amounts of sequence information (often single nucleotides) from a large number of nucleic acid samples. The so-called "minisequencing" methods are currently performed using fluorescently labeled dideoxynucleotides that are enzymatically incorporated opposite a SNP site.

Both "classical" sequencing methods and "minisequencing" methods are thus dependent upon chain terminating nucleotide analogs. The nucleotide terminators traditionally used in such methods are the dideoxy nucleotides, which are structurally similar to the "naturally occurring" deoxynucleotides but differ in the glycosyl component. The dideoxy chain terminating nucleotides contain a 2',3'-dideoxyribofuranosyl moiety.

Several acyclic nucleotides also have been used as chain terminators. Nucleotide analogs lacking the deoxyribofuranosyl moiety have been reported in the literature to function as substrates for viral DNA polymerases (e.g., Holy et al., 1990, Antiviral Res. 13: 295–312; Martinez et al., 1997, Bioorg. Med. Chem. Lett. 7: 3013–3016; Martinez et al., 1999, Nucleic Acids Res. 27: 1271–1274). The acyclic nucleoside phosphonomethoxyadenine (PME-A) has been reported to exhibit therapeutic properties in the treatment of virus-induced diseases (e.g., HSV). PME-A differs in structure from traditional nucleosides in that it has a phosphonomethoxyethyl group in place of the traditional ribofuranosyl moiety. PME-A labeled with $^{14}C$ by replacement of a $^{12}C$ atom in the adenine nucleobase was reported by Merta et al., 1990, Neoplasma 37: 111–120. The $^{14}C$-labeled PME-A was used to demonstrate that PME-A can be phosphorylated in mouse leukemia cell extracts; detection followed TLC separation of phosphorylated (PME-Ap, PME-App) from non-phosphorylated forms of PME-A.

Phosphonomethoxy carbocyclic nucleosides and nucleotides are taught by Mansuri et al., U.S. Pat. No. 5,744,600. The nucleotide analogs taught therein are said to have use as antiviral agents.

Because of increasing demand for sequencing technologies dependent upon chain terminators, there is a need in the art for alternative chain terminators, particularly for terminators that are less costly than dideoxynucleotides.

SUMMARY OF THE INVENTION

The invention relates to acyclic nucleoside analogs useful as chain terminators in enzymatic nucleic acid synthesis reactions. More particularly, the invention relates to phosphonomethoxyethyl (PME) nucleoside analogs and their use in nucleic acid sequencing reactions.

The invention encompasses a fluorescently labeled phosphonomethoxyethyl nucleotide analog.

In one embodiment, the fluorescent label is selected from the group consisting of Cy5, Cy3, TAMRA, R6G, R110, ROX, JOE, FAM, Texas Red™, Oregon Green™, squaraine dyes, oxonols, dibenzazoles, dyes absorbing in the near-IR region, near-IR heavy atom dyes, rhodamine dyes exhibiting variable fluorescent lifetimes, dichlororhodamine dyes and aromatic-substituted xanthene dyes.

In another embodiment, the nucleobase is a purine, a 7-deazapurine, a pyrimidine, or a nucleobase analog that permits the enzymatic incorporation of the nucleotide analog comprising that nucleobase analog, and is capable of forming Watson-Crick base pairs with a nucleobase on an adjacent antiparallel nucleic acid strand. A measure of whether a nucleobase analog forms a Watson-Crick base pair with a nucleobase on an adjacent polynucleotide strand is whether a nucleotide comprising that nucleobase analog is incorporated into a polynucleotide by a template-dependent nucleic acid polymerase as described herein. In a preferred embodiment, the nucleobase is selected from the group consisting of: adenine, cytosine, guanine, thymine, uracil, hypoxanthine, 7-deazapurines, pyrazolo[3,4-d]pyrimidine, imidazo[1,5-a]1,3,5 triazinones, 9-deazapurines, imidazo[4,5-d]pyrazines, thiazolo[4,5-d]pyrimidines, pyrazin-2-ones, 1,2,4-triazine, pyridazine; and 1,3,5 triazine.

In another embodiment, the fluorescent label is linked to the nucleobase moiety of the phosphonomethoxyethyl nucleotide analog.

The invention further encompasses a detectably labeled phosphonomethoxyethyl nucleotide analog having the general structure

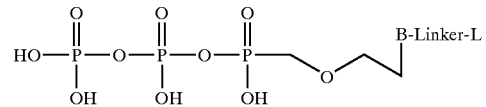

wherein L is a detectable label, and L is covalently joined to nucleobase moiety B via a linker.

In one embodiment, the linker is attached to the nucleobase at the N-4 or C-5 position of the nucleobase when the nucleobase is a pyrimidine, or at the N-6, C-8 or C(N)-7 position of the nucleobase when the nucleobase is a purine.

In another embodiment, the detectable label is selected from the group consisting of a radionuclide, a chromophore, a fluorophore, a fluorescence quencher, an enzyme, an enzyme substrate, an affinity tag, and an epitope tag recognized by an antibody.

In another embodiment, the detectable label comprises a fluorophore. In a preferred embodiment, the fluorophore is selected from the group consisting of Cy5, Cy3, TAMRA, R6G, R110, ROX, JOE, FAM, Texas Red™, Oregon Green™, squaraine dyes, oxonols, dibenzazoles, dyes absorbing in the near-IR region, near-IR heavy atom dyes, rhodamine dyes exhibiting variable fluorescent lifetimes, dichlororhodamine dyes and aromatic-substituted xanthene dyes.

In another embodiment, the nucleobase is a purine, a 7-deazapurine, a pyrimidine, or a nucleobase analog thereof capable of forming Watson-Crick base pairs with a nucleobase on an adjacent antiparallel nucleic acid strand. In a preferred embodiment, the nucleobase is selected from the group consisting of adenine, cytosine, guanine, thymine, uracil, hypoxanthine, 7-deazapurines, pyrazolo[3,4-d]pyrimidine, imidazo[1,5-a]1,3,5 triazinones, 9-deazapurines, imidazo[4,5-d]pyrazines, thiazolo[4,5-d]pyrimidines, pyrazin-2-ones, 1,2,4-triazine, pyridazine; and 1,3,5 triazine.

The invention further encompasses a phosphonomethoxyethyl nucleotide analog comprising a radionuclide replacing or covalently bound to the phosphonomethoxy phosphorus. In one embodiment, the radionuclide is selected from the group consisting of $^{32}P$, $^{33}P$ and $^{35}S$.

The invention further encompasses a method of synthesizing a polynucleotide, the method comprising contacting a nucleic acid polymerase enzyme with a phosphonomethoxyethyl nucleotide analog diphosphate, under conditions permitting the extension of a nucleic acid primer annealed to a template nucleic acid. The contacting will result in chain termination.

In one embodiment, the contacting permits the determination of nucleic acid sequence information about the template nucleic acid.

In another embodiment, the phosphonomethoxyethyl nucleotide analog is detectably labeled. In a preferred embodiment, the detectable label comprises a radionuclide, a chromophore, a fluorophore, a fluorescence quencher, an enzyme, an enzyme substrate, an affinity tag, or an epitope tag recognized by an antibody. In another preferred embodiment, the detectable label comprises a fluorophore. In another preferred embodiment, the fluorophore is selected from the group consisting of: Cy5, Cy3, TAMRA, R6G, R110, ROX, JOE, FAM, Texas Red™, Oregon Green™, squaraine dyes, oxonols, dibenzazoles, dyes absorbing in the near-IR region, near-IR heavy atom dyes, rhodamine dyes exhibiting variable fluorescent lifetimes, dichlororhodamine dyes and aromatic-substituted xanthene dyes.

In another embodiment, the detectable label is linked to the nucleobase moiety of the phosphonomethoxyethyl nucleotide analog.

In another embodiment, the nucleobase of the phosphonomethoxyethyl nucleotide analog is a purine, a 7-deazapurine, a pyrimidine, or a nucleobase analog capable of forming Watson-Crick base pairs with a nucleobase on an adjacent antiparallel nucleic acid strand. In a preferred embodiment, the nucleobase of the phosphonomethoxyethyl nucleotide analog is selected from the group consisting of adenine, cytosine, guanine, thymine, uracil, hypoxanthine, 7-deazapurines, pyrazolo[3,4-d]pyrimidine, imidazo[1,5-a]1,3,5 triazinones, 9-deazapurines, imidazo[4,5-d]pyrazines, thiazolo[4,5-d]pyrimidines, pyrazin-2-ones, 1,2,4-triazine, pyridazine; and 1,3,5 triazine.

The invention further encompasses a method of determining sequence information about a template polynucleotide, the method comprising a) annealing an oligonucleotide primer to a template polynucleotide, b) contacting the annealed primer and template of step (a) with a nucleic acid polymerase enzyme in the presence of a phosphonomethoxyethyl nucleotide analog under conditions sufficient to permit the extension of the primer by the nucleic acid polymerase enzyme, and c) detecting the incorporation of the phosphonomethoxyethyl nucleotide analog onto the primer, wherein the incorporation determines sequence information about the template polynucleotide.

In one embodiment, the method is performed on a solid support.

In another embodiment, the phosphonomethoxyethyl nucleotide analog is detectably labeled. In a preferred embodiment, the phosphonomethoxyethyl nucleotide analog is fluorescently labeled. In another preferred embodiment, the fluorescent label is selected from the group consisting of Cy5, Cy3, TAMRA, R6G, R110, ROX, JOE, FAM, Texas Red™, Oregon Green™, squaraine dyes, oxonols, dibenzazoles, dyes absorbing in the near-IR region, near-IR heavy atom dyes, rhodamine dyes exhibiting variable fluorescent lifetimes, dichlororhodamine dyes and aromatic-substituted xanthene dyes.

In another embodiment, following the completion of steps (a)–(c), steps (b) and (c) are repeated at least once more in the presence of a differentially labeled phosphonomethoxyethyl nucleotide analog, wherein the nucleobase of the nucleotide analog is different from that used in the prior execution of steps (a)–(c).

The invention further encompasses a kit comprising a phosphonomethoxyethyl nucleotide analog. In one embodiment, the phosphonomethoxyethyl nucleotide analog is a phosphonomethoxyethyl diphosphate nucleotide analog. In another embodiment, the kit further comprises a nucleic acid polymerase and/or an oligonucleotide primer. In a preferred embodiment, the phosphonomethoxyethyl nucleotide analog in the kit is detectably labeled. In one embodiment, the detectable label is selected from the group consisting of a radionuclide, a chromophore, a fluorophore, a fluorescence quencher, an enzyme, an enzyme substrate, an affinity tag, and an epitope tag recognized by an antibody. In a preferred embodiment, the detectable label comprises a fluorophore. In a further preferred embodiment, the fluorophore is selected from the group consisting of Cy5, Cy3, TAMRA, R6G, R110, ROX, JOE, FAM, Texas Red™, Oregon Green™, squaraine dyes, oxonols, dibenzazoles, dyes absorbing in the near-IR region, near-IR heavy atom dyes, rhodamine dyes exhibiting variable fluorescent lifetimes, dichlororhodamine dyes and aromatic-substituted xanthene dyes.

In another embodiment, the nucleobase of the nucleoside analog is a purine, a 7-deazapurine, a pyrimidine, or a nucleobase analog capable of forming Watson-Crick base pairs with a nucleobase on an adjacent antiparallel nucleic acid strand. In a preferred embodiment, the nucleobase of the nucleoside analog is selected from the group consisting of adenine, cytosine, guanine, thymine, uracil, hypoxanthine, 7-deazapurines, pyrazolo[3,4-d]pyrimidine, imidazo[1,5-a]1,3,5 triazinones, 9-deazapurines, imidazo[4,5-d]pyrazines, thiazolo[4,5-d]pyrimidines, pyrazin-2-ones, 1,2,4-triazine, pyridazine; and 1,3,5 triazine.

In another embodiment, the detectable label comprises a radionuclide. In a preferred embodiment, the detectable label comprises a radionuclide covalently linked to the phosphorus atom of the phosphonomethoxy group. In another preferred embodiment, the radionuclide is $^{35}S$. In another preferred embodiment, the phosphorus in the phosphonomethoxy moiety consists of $^{32}P$ or $^{33}P$.

Definitions:

As used herein, the term "phosphonomethoxyethyl nucleotide analog" or the equivalent term "PME nucleotide analog" refers to a molecule of general structure:

(Structure 1)

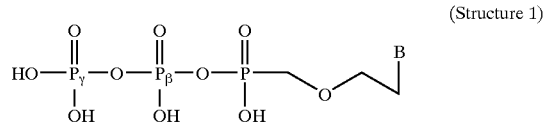

where B represents a purine, 7-deazapurine or pyrimidine nucleobase or a nucleobase analog that permits Watson-Crick base pairing between the analog and the nucleobase of a nucleotide on an adjacent antiparallel oligo- or polynucleotide. The nucleobase moiety B is preferably selected from the group consisting of adenine, cytosine, guanine, thymine, uracil and hypoxanthine, although modified forms and functional analogs of these are specifically contemplated (see below). The phosphorus atom proximal to the phosphonomethoxy moiety is referred to herein as the "beta" phosphorus. The phosphorus atom next to the P phosphorus and more distal to the phosphonomethoxy moiety is referred to herein as the "gamma phosphorus." The term "phosphonomethoxyethyl nucleotide analog" is intended to encompass molecules of the general structure above wherein the phosphorus of the phosphonomethoxy group is radiolabeled (i.e., $^{32}P$ or $^{33}P$) and in which the phosphorus of the phosphonomethoxyethyl group is linked to $^{35}S$. The PME nucleotide analog according to the invention will serve as a substrate for a nucleic acid polymerase enzyme to produce a PME nucleotide analog covalently attached to the 3' end of a nucleic acid primer annealed to a template nucleic acid strand. The PME nucleotide analog according to the invention will be incorporated opposite, and hydrogen bond with, a complementary nucleotide on the template strand. Further, a PME nucleotide analog according to the invention will act as a chain terminator for the template-directed polymerization of a polynucleotide by a nucleic acid polymerase.

As used herein, the term "complementary nucleotide" refers to a nucleotide in which, when conditions permit the annealing or hybridization of nucleic acid strands, the nucleobase of the nucleotide forms hydrogen bonds with the nucleobase of a given PME nucleotide analog. The pattern of hydrogen bond formation between the respective complementary nucleobases will be as follows: adenine hydrogen bonding to thymine or uracil (two H bonds), guanine hydrogen bonding to cytosine (three H bonds), and hypoxanthine hydrogen bonding to adenine, cytosine or uracil (hypoxanthine is the nucleobase moiety of the ribonucleoside inosine).

As used herein, the term "nucleobase" refers to the heterocyclic nitrogenous base of a nucleotide or nucleotide analog. Nucleobases useful according to the invention include, but are not limited to adenine, cytosine, guanine, thymine, uracil, and hypoxanthine. Additional nucleobases that can be comprised by a PME nucleotide analog according to the invention include, but are not limited to naturally-occurring and synthetic derivatives of the preceding group, for example, pyrazolo[3,4-d]pyrimidines, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine, 3-deazaadenine, pyrazolo[3,4-d]pyrimidine, imidazo[1,5-a]1,3,5 triazinones, 9-deazapurines, imidazo[4,5-d]pyrazines, thiazolo[4,5-d]pyrimidines, pyrazin-2-ones, 1,2,4-triazine, pyridazine; and 1,3,5 triazine. Nucleobases useful according to the invention will permit a nucleotide bearing that nucleobase to be enzymatically incorporated into a polynucleotide chain and will form Watson-Crick base pairs with a nucleobase on an antiparallel nucleic acid strand.

As used herein, the phrase "Watson-Crick base pair" refers to a pair of hydrogen-bonded nucleobases on opposite antiparallel strands of nucleic acid. The well-known rules of base pairing first elaborated by Watson and Crick, require that adenine (A) pairs with thymine (T) or uracil (U), and guanine (G) pairs with cytosine (C), with the complementary strands anti-parallel to one another. The Watson-Crick pairing rules can be understood chemically in terms of the arrangement of hydrogen bonding groups on the heterocyclic bases of the oligonucleotide, groups that can either be hydrogen bond donors or acceptors. In the standard Watson-Crick geometry, a large purine base pairs with a small pyrimidine base; thus, the AT base pair is the same size as a GC base pair. This means that the rungs of the DNA ladder, formed from either AT or GC base pairs, all have the same length. Further recognition between bases is determined by hydrogen bonds between the bases. Hydrogen bond donors are heteroatoms (nitrogen or oxygen in the natural bases) bearing a hydrogen; hydrogen bond acceptors are heteroatoms (nitrogen or oxygen in the natural bases) with a lone pair of electrons. In the geometry of the standard Watson-Crick base pair, a six membered ring (in natural oligonucleotides, a pyrimidine) is juxtaposed to a ring system composed of a fused six membered ring and a five membered ring (in natural oligonucleotides, a purine), with a middle hydrogen bond linking two ring atoms, and hydrogen bonds on either side joining functional groups appended to each of the rings, with donor groups paired with acceptor groups.

As used herein, the term "Watson-Crick base pair" encompasses not only the standard AT, AU or GC base pairs, but also base pairs formed between nucleobases of nucleotide analogs comprising non-standard or modified nucleobases, wherein the arrangement of hydrogen bond donors and hydrogen bond acceptors permits hydrogen bonding between a non-standard nucleobase and a standard nucleobase or between two complementary non-standard nucleobase structures. One example of such non-standard Watson-Crick base pairing is the base pairing engaged in by the nucleotide analog inosine, wherein the hypoxanthine nucleobase forms two hydrogen bonds with adenine, cytosine or uracil.

As used herein, the phrase "nucleobase analog capable of forming Watson-Crick base pairs with a nucleobase on an adjacent antiparallel nucleic acid strand" refers to a nucleobase other than one of adenine, cytosine, guanine, thymine and uracil, that, when incorporated into an oligo- or polynucleotide strand has hydrogen bond donors or acceptors located such that the nucleobase can form hydrogen bonds with hydrogen bond acceptors or donors, respectively, present on a nucleobase or nucleobase analog on an adjacent antiparallel nucleic acid strand. U.S. Pat. No. 6,001,983, which is incorporated herein by reference, provides guidance on the design of nucleobase analogs capable of forming non-standard Watson-Crick base pairs, and methods of analyzing their base pair interactions. A "nucleobase analog capable of forming Watson-Crick base pairs with a nucleobase on an adjacent antiparallel nucleic acid strand" useful according to the invention will permit the template-dependent enzymatic incorporation of a nucleotide analog comprising such a nucleobase analog into a polynucleotide chain.

As used herein, the term "detectable label" refers to a moiety that can be directly or indirectly detected. Detectable labels include, but are not limited to radionuclides (e.g., $^{32}P$, $^{33}P$, $^{35}S$, etc.), chromophores, fluorophores, fluorescence quenchers, enzymes, enzyme substrates, affinity tags (e.g., biotin, avidin, streptavidin, etc.), and epitope tags recognized by an antibody. As used herein, a "directly detectable" label can be measured without requirement for additional substrates or binding partners. Examples of directly detectable labels include radionuclides and fluorophores. As used herein, an "indirectly detectable" label requires reaction or interaction with another substrate or reagent for detection. Examples of indirectly detectable labels include enzymes (requires substrate), enzyme substrates (requires enzyme), affinity tags (requires affinity partner), and epitope tags (requires antibody).

As used herein, the phrase "differentially labeled" means that one entity is labeled with a first detectable moiety and another entity is labeled with a second detectable moiety, and that the signals from the first and second detectable moieties can be distinguished. A "distinguishable fluorescent label" refers to a fluorescent label in which the emission peak can be distinguished from another fluorescent label present in the same mixture; generally, if the peak emission wavelengths of two fluorophores differ by at least 20 nm, they are considered to be distinguishable fluorophores.

As used herein, the phrase "wherein the label is linked to the nucleobase" means that the labeling moiety is linked to the nucleobase of the PME nucleotide analog, rather than replacing an atom of the structure of the nucleobase. For example, in a PME nucleoside analog labeled by the incorporation of a radionuclide (e.g., $^{14}C$ or $^{15}N$) into the structure of the nucleobase, the label is not "linked to the nucleobase." In contrast, a fluorophore appended to the nucleobase via an allyl amine group or other linking group attached to the nucleobase is "linked to the nucleobase." Linkers useful according to the invention are described herein below.

As used herein, the term "chain terminator" refers to a nucleotide analog that serves as a substrate for a nucleic acid polymerase enzyme, but once incorporated onto the end of a growing polynucleotide chain, the analog cannot itself serve as a substrate for the attachment of subsequent nucleotide residues. Classic examples of chain terminators include the dideoxynucleoside triphosphates ddA, ddC, ddG, and ddT. PME nucleotide analogs according to the invention are chain terminators.

As used herein, the phrase "determining sequence information" refers to the process wherein at least one nucleotide in a polynucleotide sequence is identified. Thus, the phrase "determining sequence information" encompasses both "classical" chain terminator sequencing ("Sanger method," Sanger et al., 1975, *J. Mol. Biol.*, 94:441), which can provide the sequences of hundreds to thousands of contiguous nucleotides in a single set of reactions, as well as the so-called "minisequencing" methods useful for identifying, for example, single base differences in a sequence relative to a standard.

As used herein, the phrase "nucleic acid polymerase enzyme" refers an enzyme that catalyzes the template-dependent polymerization of nucleoside triphosphates to form primer extension products that are complementary to one of the nucleic acid strands of the template nucleic acid sequence. A nucleic acid polymerase enzyme initiates synthesis at the 3' end of an annealed primer and proceeds in the direction toward the 5' end of the template. Numerous nucleic acid polymerases are known in the art and commercially available. Preferred nucleic acid polymerases are thermostable, i.e., they retain function after being subjected to temperatures sufficient to denature annealed strands of complementary nucleic acids.

As used herein, the phrase "conditions permitting the extension of a nucleic acid primer annealed to a template nucleic acid" refers to those conditions of salt concentration (metallic and non-metallic salts), pH, temperature, and necessary cofactor concentration under which a given polymerase enzyme catalyzes the extension of an annealed primer. Conditions for the primer extension activity of a wide range of polymerase enzymes are known in the art. As one example, conditions permitting the extension of a nucleic acid primer by Taq polymerase include the following (for any given enzyme, there can and often will be more than one set of such conditions): reactions are conducted in a buffer containing 50 mM KCl, 10 mM Tris (pH 8.3), 4 mM $MgCl_2$, (200 µM of one or more dNTPs and/or a chain terminator may be included, depending upon the type of primer extension or sequencing being performed); reactions are performed at 72° C.

As used herein, the term "affinity tag" refers to a moiety that can be attached to a nucleoside or nucleoside analog, and that is specifically bound by a partner moiety. The interaction of the affinity tag and its partner provides for the detection of molecules bearing the affinity tag. Examples include, but are not limited to biotin or iminobiotin and avidin or streptavidin. A sub-class of affinity tag is the "epitope tag," which refers to a tag that is recognized and specifically bound by an antibody or an antigen-binding fragment thereof. Examples of epitope tags include the Myc tag (peptide EQKLISEEDL (SEQ ID NO: 1), recognized by monoclonal anti-Myc antibodies 9E10, 9B11), Flag™ tag (peptide DYKDDDDK (SEQ ID NO: 2), recognized by anti-Flag™ antibody; Chubet & Brizzard (1996) Biotechniques 20:136–141), and digoxigenin (recognized by anti-digoxigenin antibody).

As used herein, the term "spectrally distinguishable fluorescent dyes" refers to fluorescent dyes that emit fluorescent energy at wavelengths that can be distinguished by fluorescent detection equipment (for example, the ABI Prism™ 377 Sequencer) when two or more such dyes are present in one sample. An example of a set of spectrally distinguishable fluorescent dyes useful for nucleotide sequencing reactions is rhodamine-6G (R6G), rhodamine 110 (R110), tetramethyl rhodamine (TAMRA) and rhodamine X (ROX) (available from Molecular Probes, Eugene, Oreg.). Another set of other spectrally distinguishable fluorescent dyes include, for example, the variants dichloro-R6G, dichloro-ROX, dichloro-R110 and dichloro-TAMRA (Applied Biosystems, Inc., Foster City, Calif.).

DETAILED DESCRIPTION OF THE INVENTION

Figure 1:
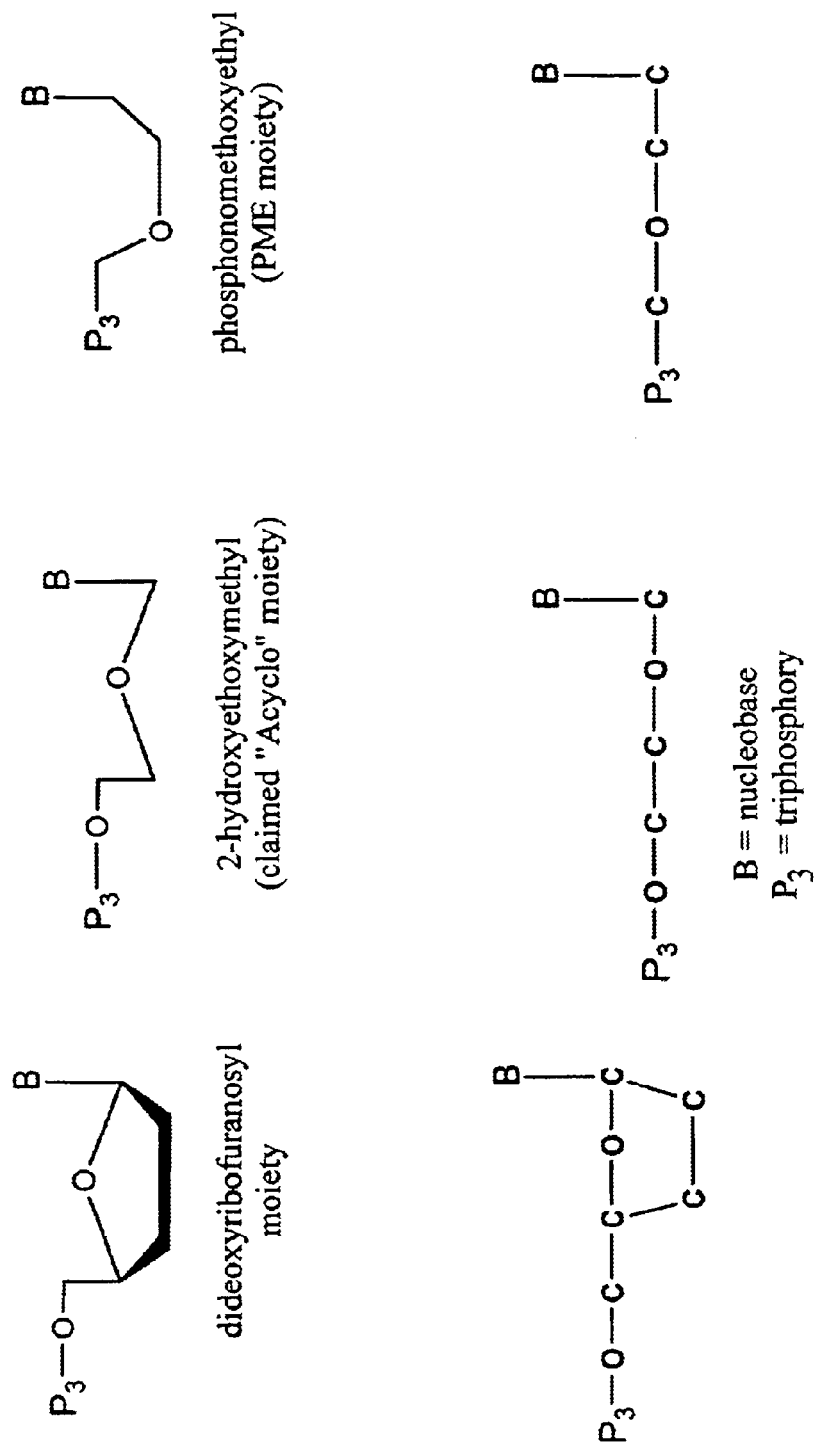
FIG. 1 shows a structural comparison of the "sugar" subunits found in chain terminator nucleotides and nucleotide analogs.

All literature and patent references referred to herein are incorporated herein in their entirety.

Phosphonomethoxyethyl Nucleotide Analogs Useful According to the Invention

The invention relates to acyclic nucleotide analogs of the general structure:

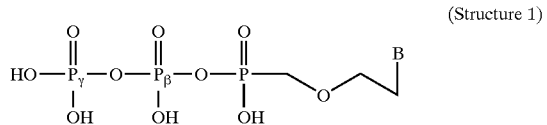

(Structure 1)

where B represents a purine, 7-deazapurine or pyrimidine nucleobase or a nucleobase analog thereof that permits Watson-Crick base pairing between the analog and the nucleobase of a nucleotide on an adjacent antiparallel oligo- or polynucleotide (e.g., a heterocyclic ring system substituted with amino or hydroxyl groups necessary for successful Watson-Crick base pairing). Nucleobase moiety B is preferably selected from the group consisting of adenine, cytosine, guanine, thymine, uracil and hypoxanthine, although modified forms of these are specifically contemplated. More specifically, the invention relates to detectably labeled phosphonomethoxyethyl (PME) nucleotide analogs of the general structure:

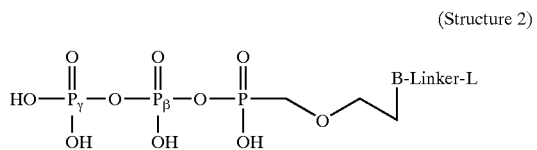

(Structure 2)

wherein "Linker" is a linker moiety as described herein and "L" is a detectable label attached to the nucleobase moiety B via the Linker. Suitable detectable labels include those known in the art to be useful for nucleic acid labeling, but are preferably radionuclides or fluorophores.

PME nucleotide analogs according to the invention are recognized and incorporated onto an annealed primer by a nucleic acid polymerase. The incorporation of a PME nucleotide analog according to the invention results in chain termination by the polymerase because the incorporated analog cannot serve as a substrate for further nucleotide addition.

PME nucleotide analogs useful according to the invention include, but are not limited to PME nucleotide analogs bearing the "traditional" nucleobase moieties, e.g., PME-adenine diphosphate (PME-App), PME-cytosine diphosphate (PME-Cpp), PME-guanine diphosphate (PME-Gpp) and PME-thymine diphosphate (PME-Tpp). In addition to these "traditional" nucleobase moieties, the invention contemplates the use of variant nucleobases that either occur naturally or were synthetically derived from a naturally-occurring nucleobase moiety. A non-exclusive listing of examples of variant nucleobase moieties contemplated includes uracil, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substitute adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine, 3-deazaadenine, and pyrazolo[3,4-d]pyrimidine. Additional non-standard nucleobase analogs capable of forming Watson-Crick base pairs are described in U.S. Pat. No. 6,001,983, which is incorporated herein by reference.

Other alternative nucleobase moieties useful according to the invention, in addition to 7-deazapurines, include the following alternative ring systems:

A) Additional alternatives to the purine ring system include, but are not limited to imidazo[1,5-a]1,3,5 triazinones (e.g., synthesized as described by Leonard, N. J., et al, 1979, J. Org. Chem. 44: 1740–1742); 9-deazapurines (synthesized as described by Cottam, H. B., et al, 1990, J. Med. Chem. 33: 2750–55); adenosine analogs in the pyrrolo[2,3-d]pyridazine ring system as described by Montgomery, J. A., et al, 1992, J. Med. Chem. 35: 533–538); imidazo[4,5-d]pyrazine (synthesized as described by Holy, A., et al., 1999, J. Med. Chem. 42: 2064–2086); pterin analogs (e.g,. as described by Pfleiderer, W., et al, 1995, Nucleic Acids Res. 23: 2872–2880); and analogs containing heteroatoms in the ring (e.g., thiazolo[4,5-d]pyrimidines synthesized as described by H. B. Cottam, et al., 1990, J. Med. Chem., 33: 407–415); and B) Pyrimidine-like alternatives include, but are not limited to: pyridine analogs (synthesized as described by Holy, A., et al., 1999, J. Med. Chem. 42: 2064–2086 and Benner, S. A., et al, 1991, Helv. Chem. Acta, 74: 397–406); pyrazin-2-one analogs (synthesized as described by Benner, S. A., et al, 1996, Helv. Chem. Acta 79: 1863–1881); analogs of 1,2,4-triazine (synthesized as described by Holy, A., et al., 1999, J. Med. Chem. 42: 2064–2086); pyridazine; and 1,3,5 triazine.

Any of the nucleobase moieties described herein or others known in the art can be used in a PME nucleotide analog according to the invention, as long as the resulting nucleotide analog serves as a substrate for and is incorporated into a primer by one or more nucleic acid polymerases and results in chain termination by such nucleic acid polymerase. Methods to test a given nucleotide analog for incorporation and chain termination are known in the are and described herein below.

In addition to a linker arm used to attach a detectable moiety (e.g., a fluorophore), the nucleobase of the PME nucleotide analogs useful according to the invention can also be substituted with amino or hydroxyl (oxo tautomer) groups necessary for successful Watson-Crick base pairing. When a ring system other than a purine or pyrimidine is used, the amino and hydroxyl groups must be positioned on the ring so that successful base pairing can still occur, ie., they must be positioned to be structurally equivalent to the corresponding substituents on the naturally-occurring purine/pyrimidine ring.

Linkers Useful According to the Invention

The linker arm can be attached to the nucleobase at any position that does not interfere with the ability of the nucleobase to participate in Watson-Crick base pairing. For example, linker arm attachment at the N-4 or C-5 position of pyrimidines is acceptable (See the PME-T and PME-C analogs in FIG. 2). An alternative structure for a "T" analog, termed "PME-ψ" in FIG. 3(e), has the linker arm attached at N-1(3), which is spatially equivalent to C-5. The linker arm can be attached to purines at either N-6, C-8 or C(N)7. When an alternative ring system is chosen (such as pyrazolo [3,4-d]pyrimidine) the linker should be positioned to be structurally equivalent to the acceptable positions on a purine nucleotide (see for example, the C-3-alkenyl-Fluor-PME-pyrazolo[3,4-d]pyrimidine in FIG. 2(d)).

One common way to add a fluorescent label to a target molecule is to react an NHS ester of the dye with a reactive amino group on the target. Nucleotides can be modified to carry a reactive amino group by, for example, inclusion of an allyl amine group on the nucleobase. Labeling via allyl amine is described, for example, in U.S. Pat. Nos. 5,476,928 and 5,958,691, which are incorporated herein by reference. While any nucleotide can be allyl amine modified, dUTP, dGTP and dTTP are perhaps best suited for situations, such as sequencing, in which maintenance of the natural hydrogen bonding capacity is called for dUTP is modified by placing the aminoallyl group on the C5 position of the nucleobase. This position does not participate in hydrogen bonding necessary for nucleic acid heteroduplex formation. In contrast, dATP and dCTP are generally modified at the C6 position and the C4 position of the nucleobases, respectively. These sites do participate in hydrogen bonding in the heteroduplex, which makes them less attractive as sites for linker-mediated labeling.

A variety of linkers are useful for joining a detectable moiety (e.g., a fluorescent dye) to PME nucleotide analogs useful according to the invention. For clarity, the detectable moiety referred to herein below is a fluorescent dye, but it should be understood that other types of detectable moieties with similar reactive groups can also be used. As used herein, the term "linker" refers to the chemical group or groups that join a detectable moiety, e.g., a fluorescent dye, to a PME nucleotide analog. The labeled PME nucleotide analog can be generated by reacting a PME nucleotide, modified on the nucleobase to contain a reactive group (e.g., an amine on an allyl amine or alkynyl amine), with a fluorescent dye bearing a complementary reactive group (e.g., a succinimidyl (NHS) group). Alternatively, the PME nucleotide, modified to contain a reactive group on the nucleobase, can be reacted first with an intermediate linker moiety, such as an ethylene oxy group, and then reacted with a fluorescent dye with an appropriate reactive group (e.g., an NHS group). In either instance, the "linker" according to the invention is considered to be the chemical entity or entities between the nucleobase and the fluorescent dye. That is, the "linker" encompasses any modifying group added to the nucleobase in order to provide a reactive group for the attachment of an intermediate linking group, and any such intermediate linking group.

Figures 2, 2A:
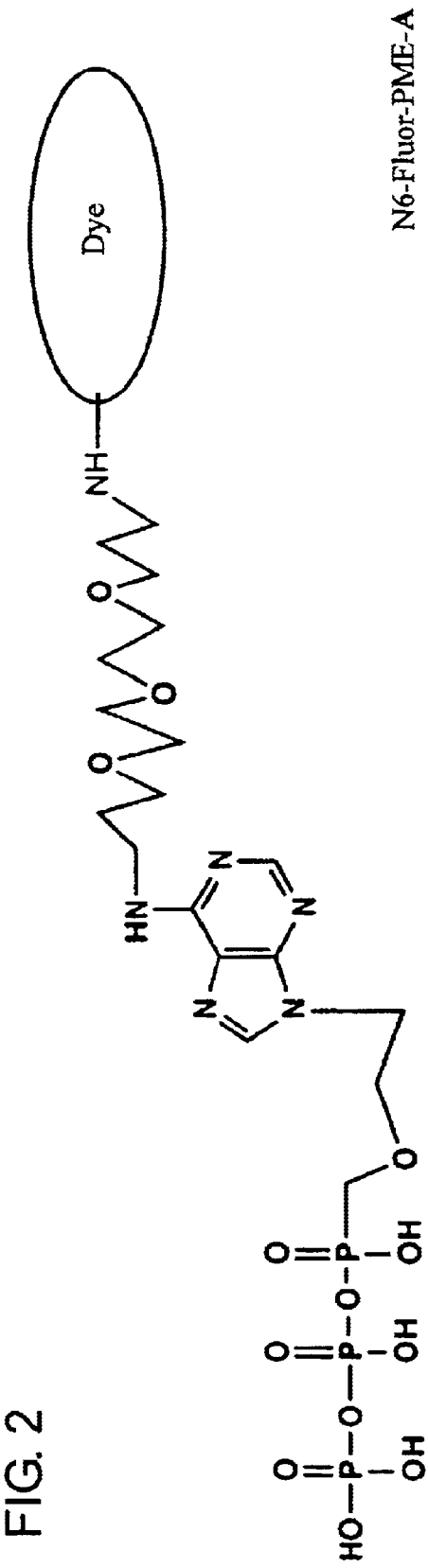
FIG. 2 schematically shows a set of fluorescent dye-labeled PME nucleotide diphosphate analog chain terminators according to the invention.
Figure 2B:
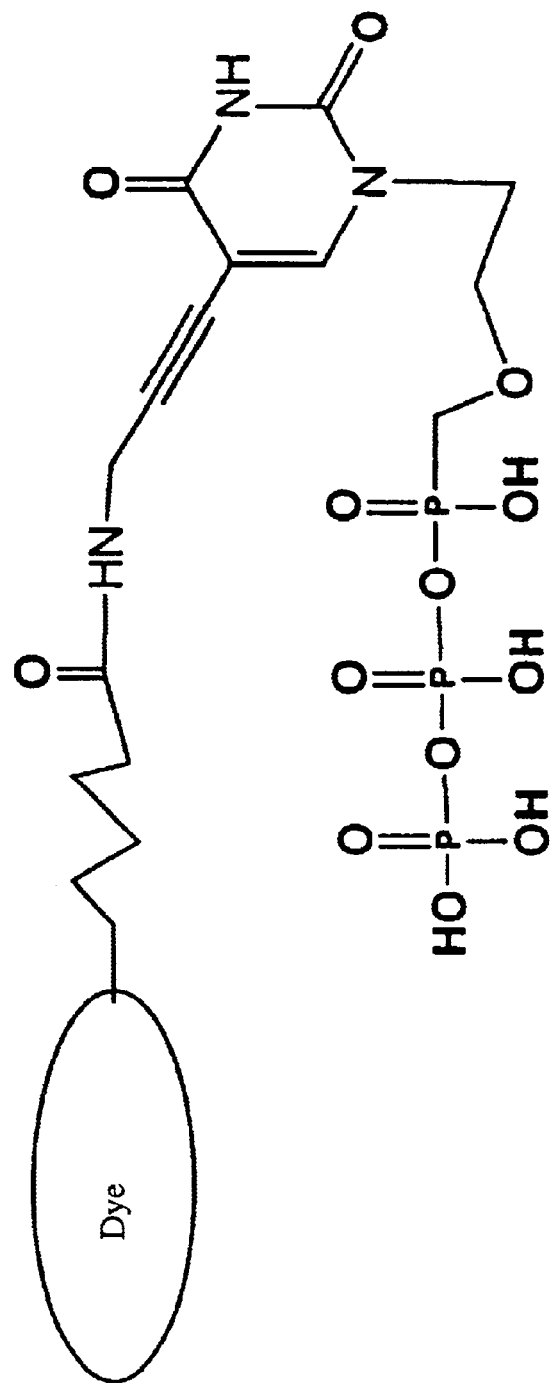
Figure 2C:
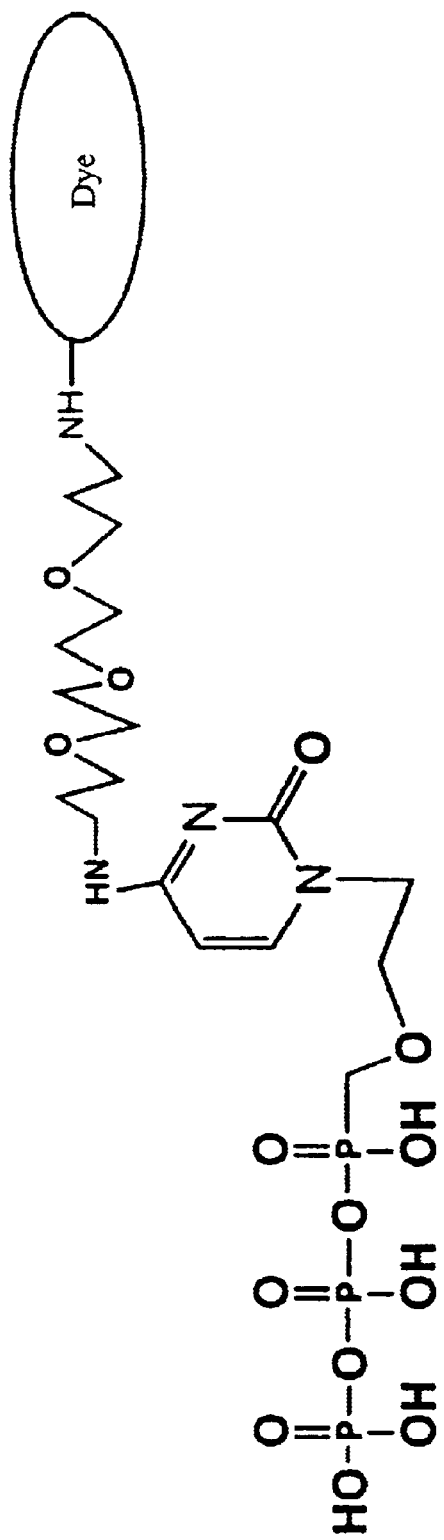
Figure 2D:
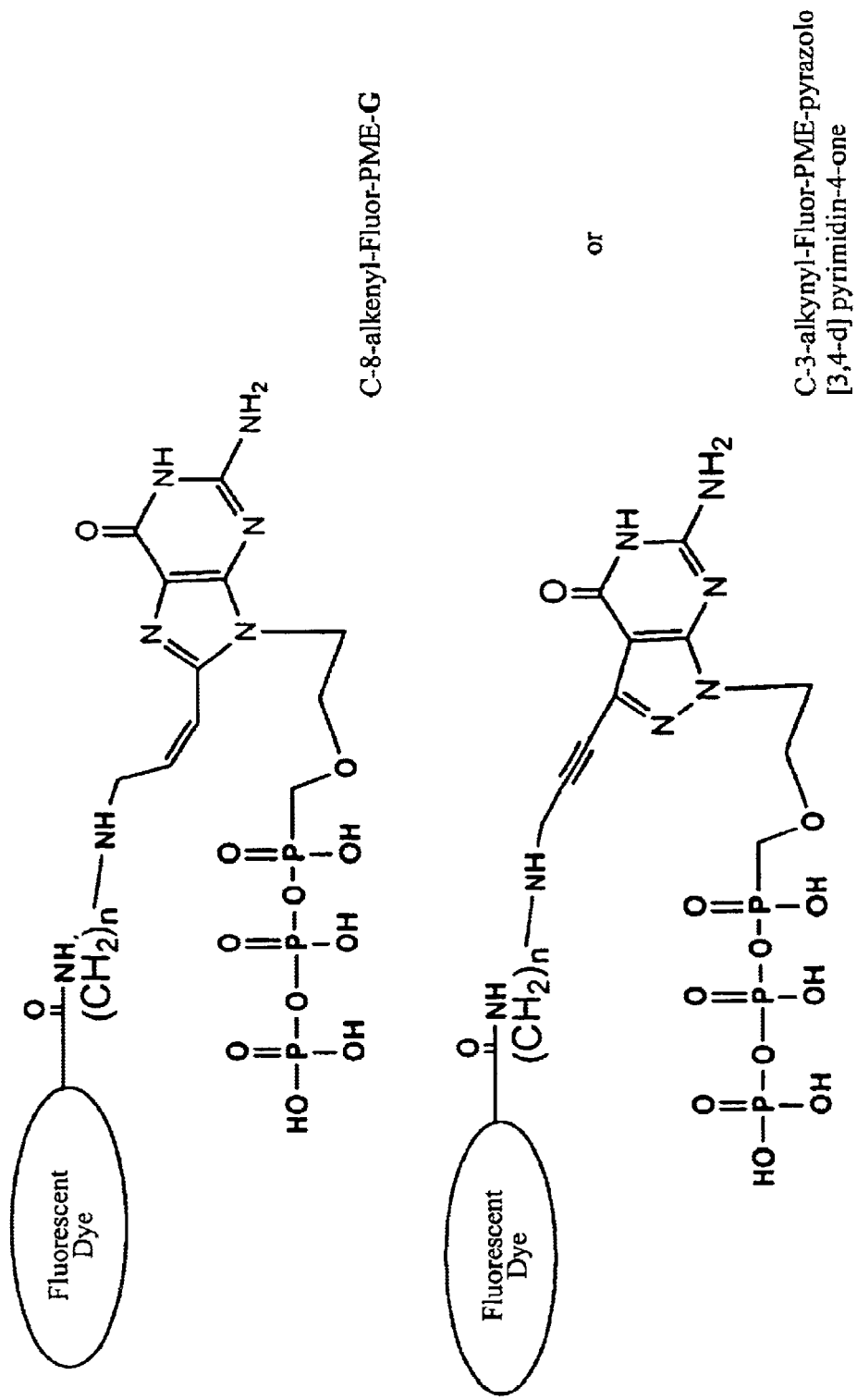
Figures 3, 3A:
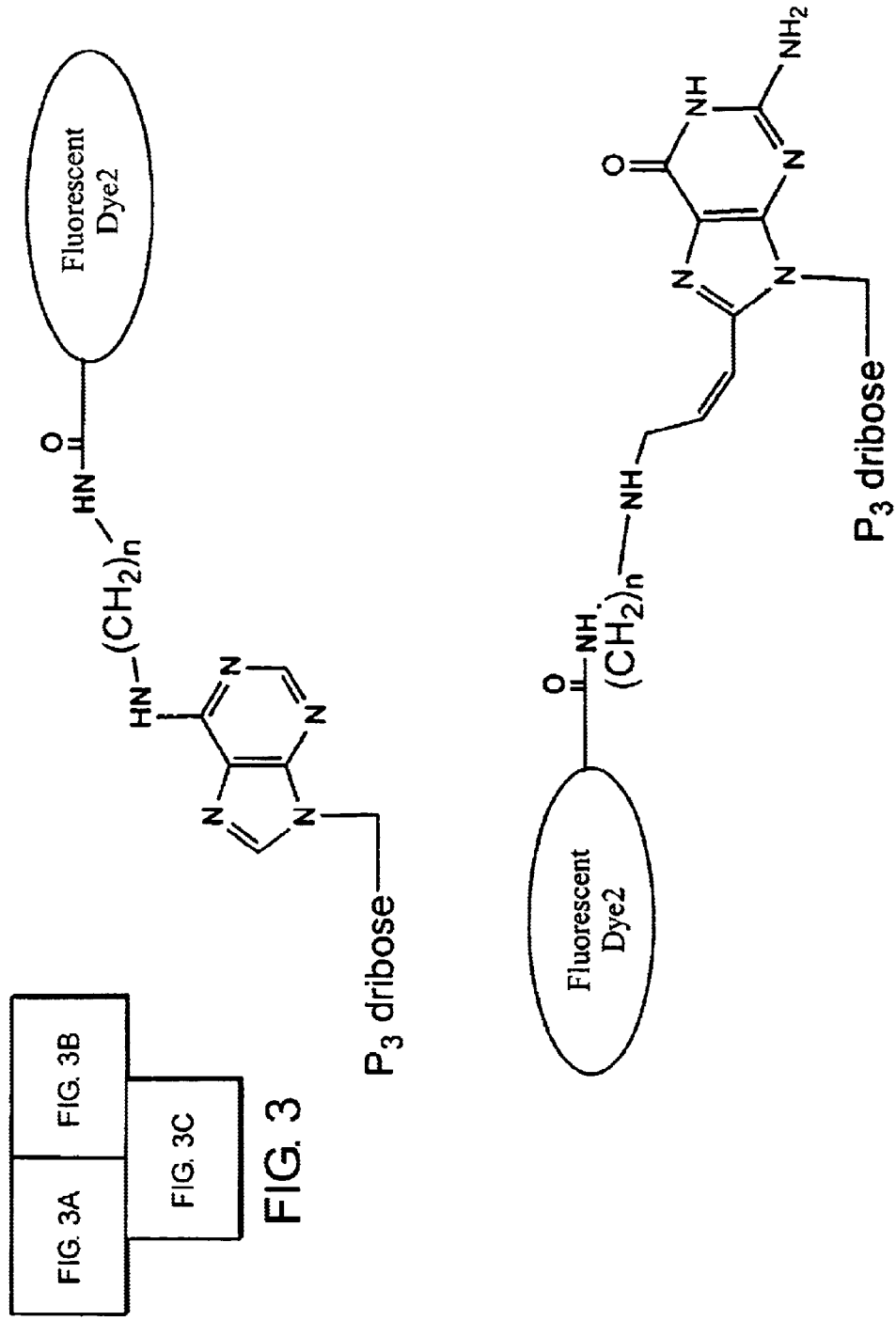
FIG. 3 schematically shows several representative variations on linkers and points of attachment for fluorescent labels on nucleobase moieties.
Figure 3B:
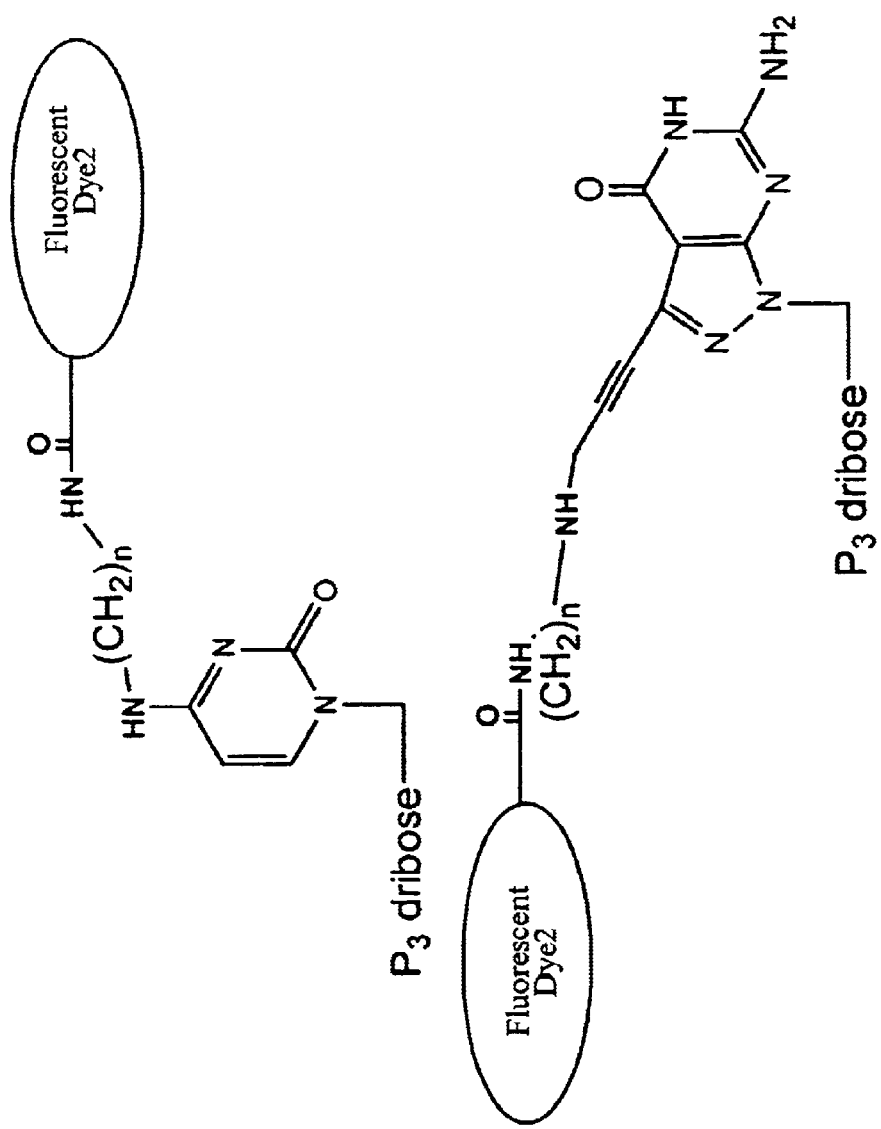
Figure 3C:
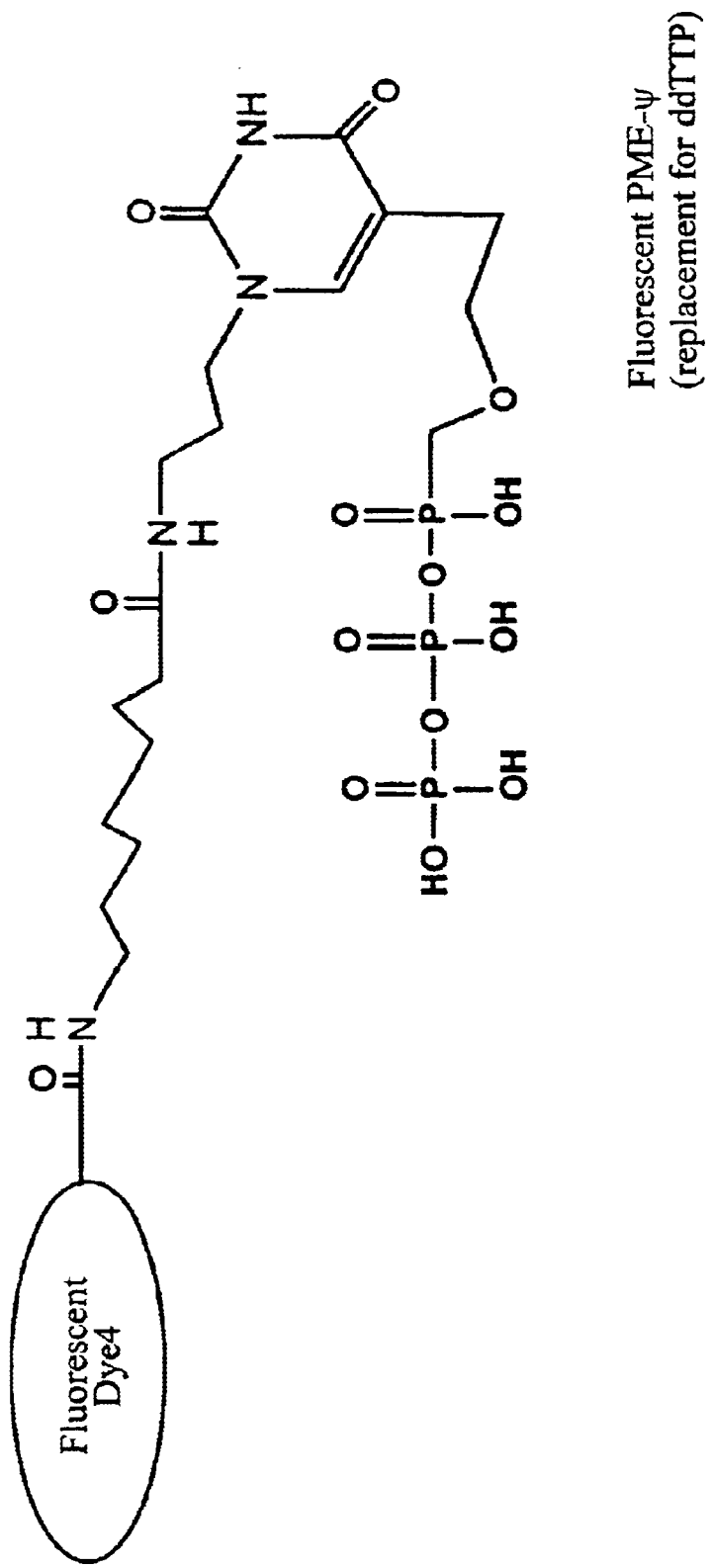
Figure 4B:
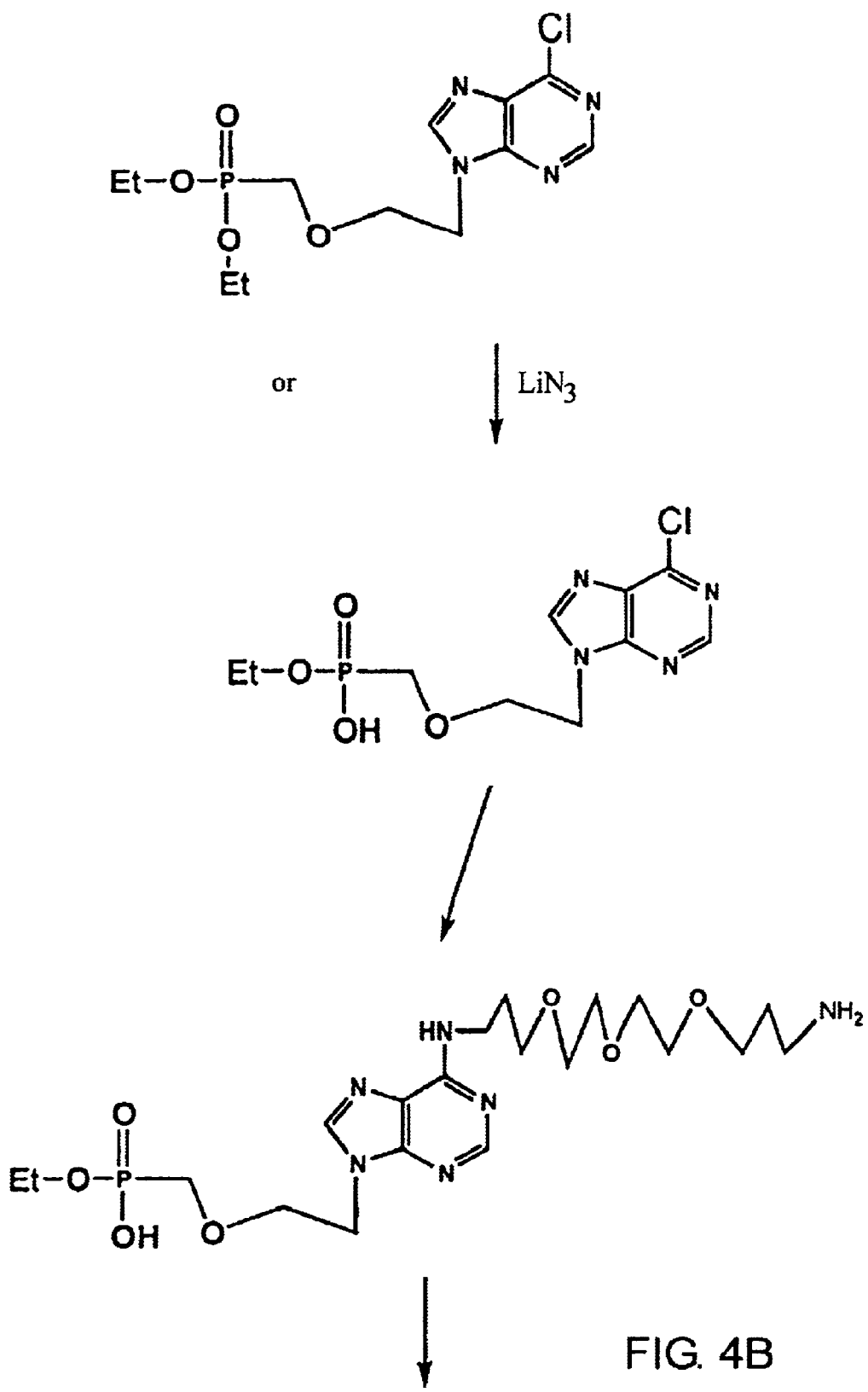
FIG. 4 schematically shows steps in two alternative pathways for the synthesis of fluorescently-labeled PME-App.
Figure 4C:
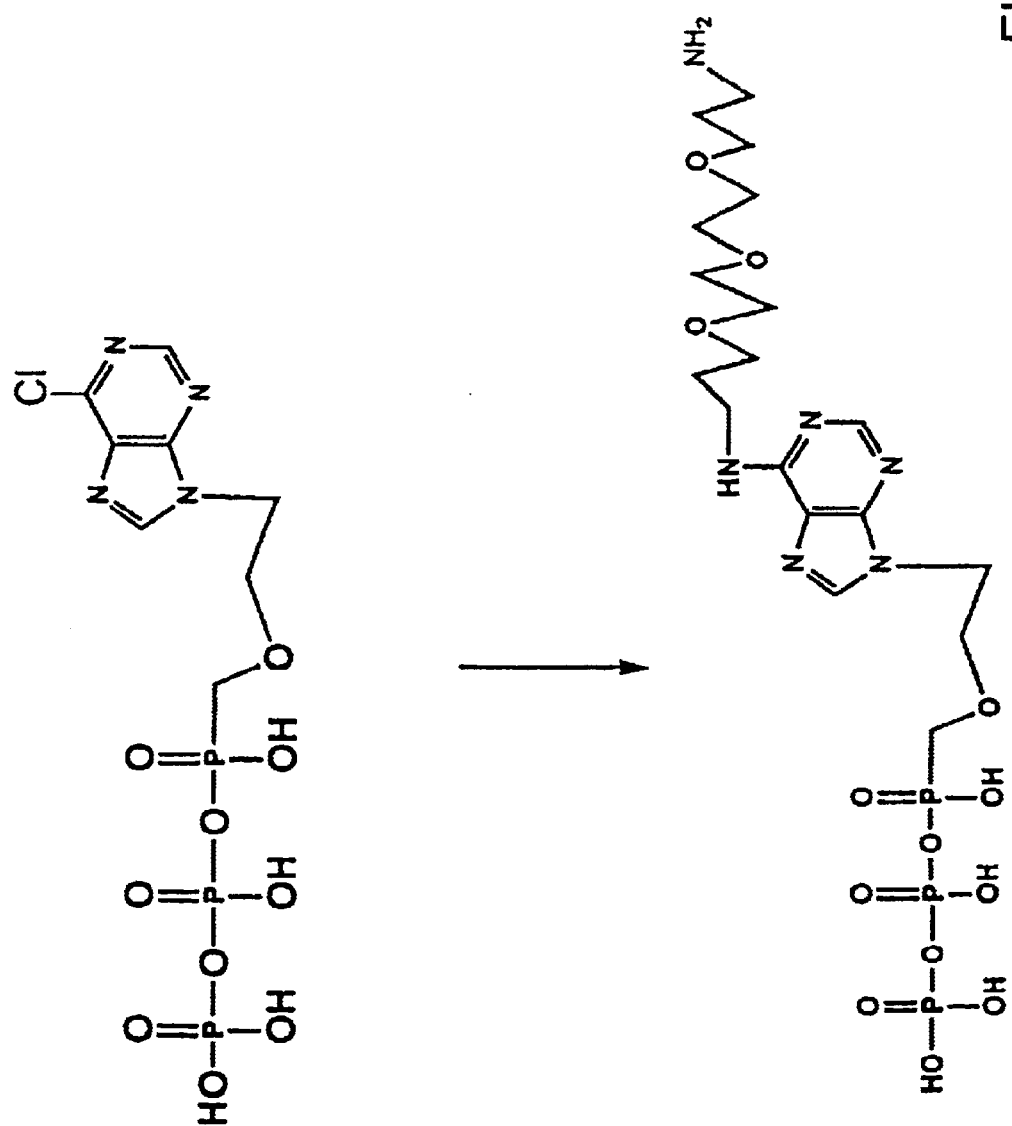
Figure 4D:
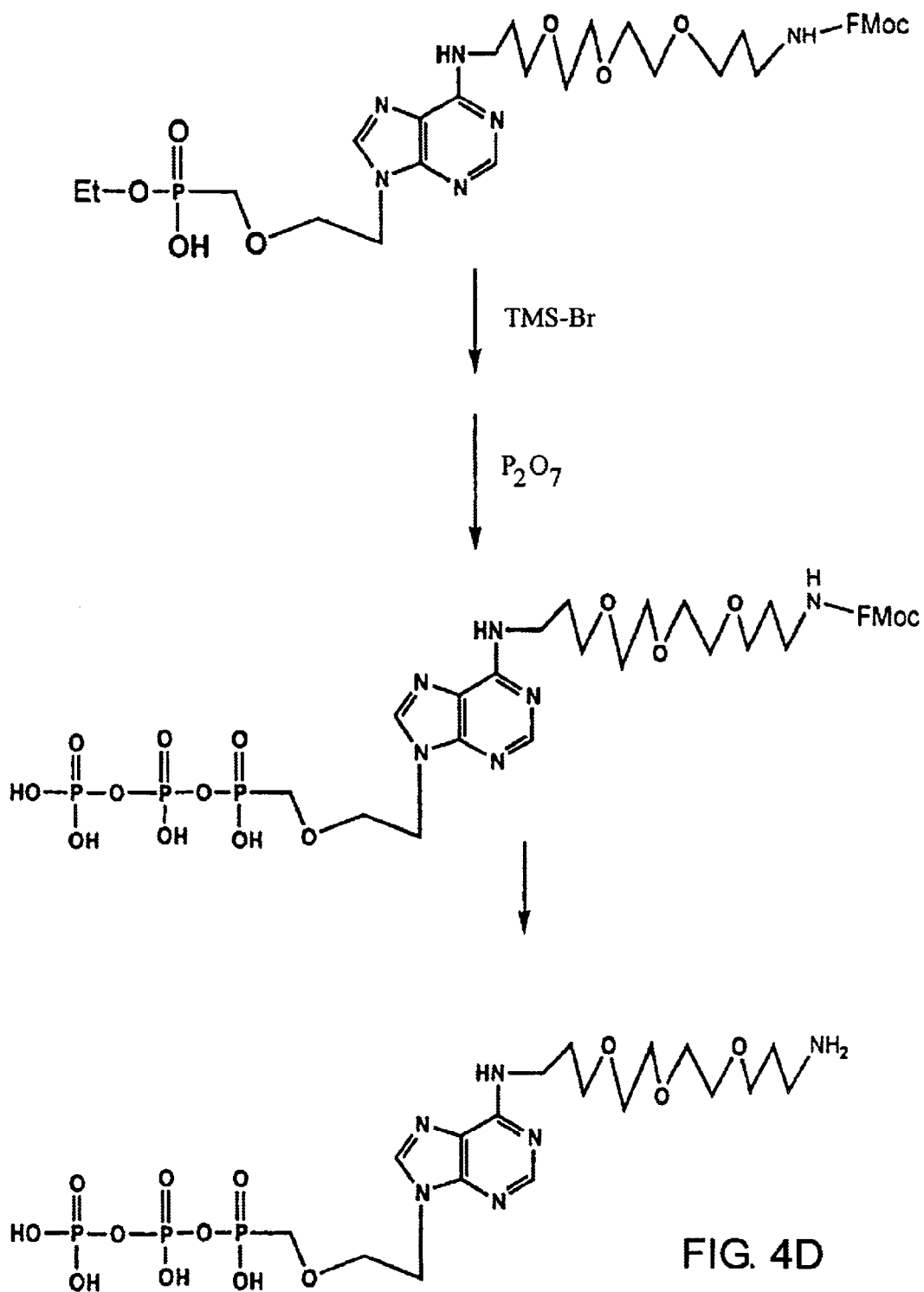
Figures 4E, 5:
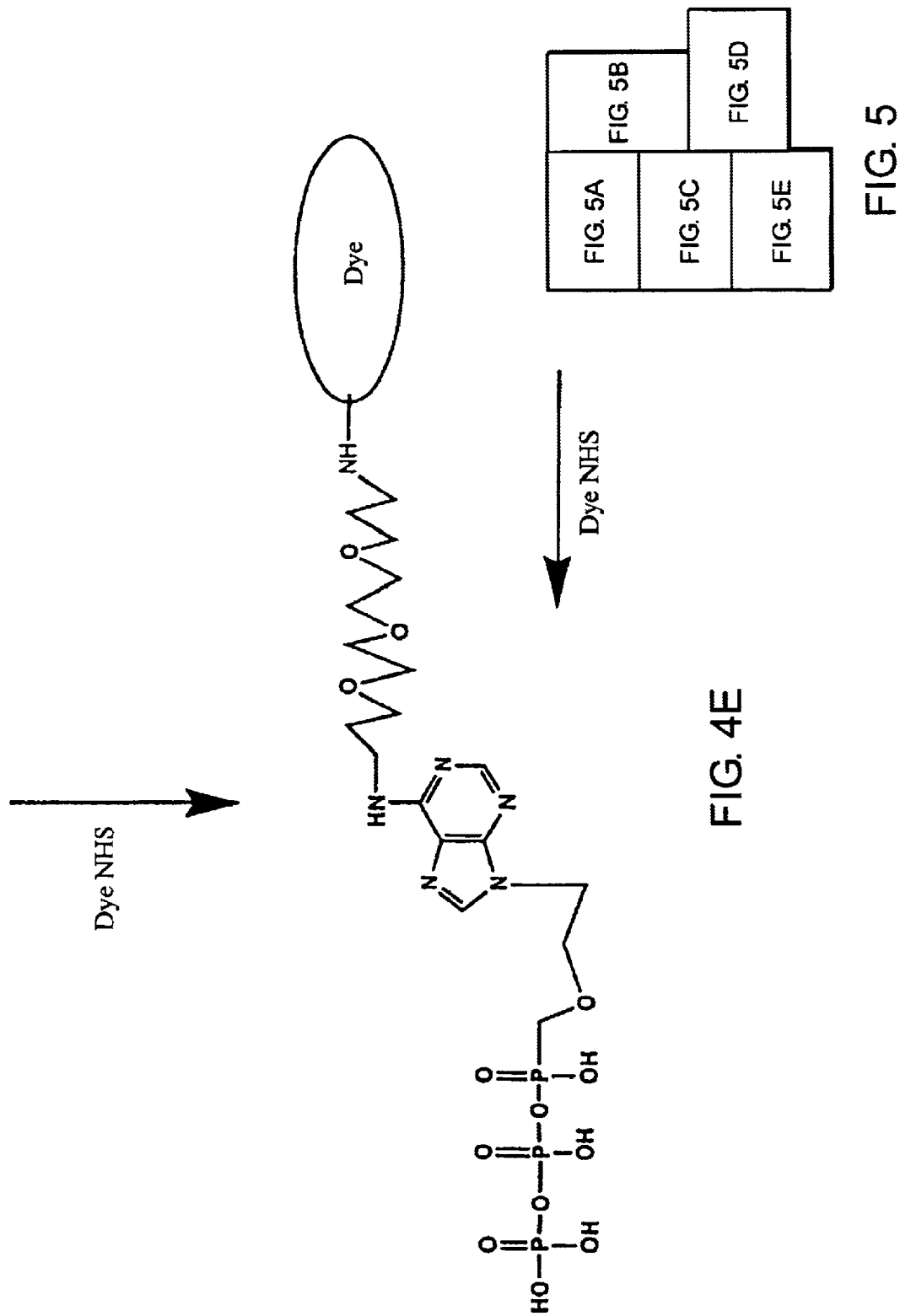
FIG. 5 schematically shows steps in a synthesis pathway for PME-Cpp nucleotide analog.
Figure 5B:
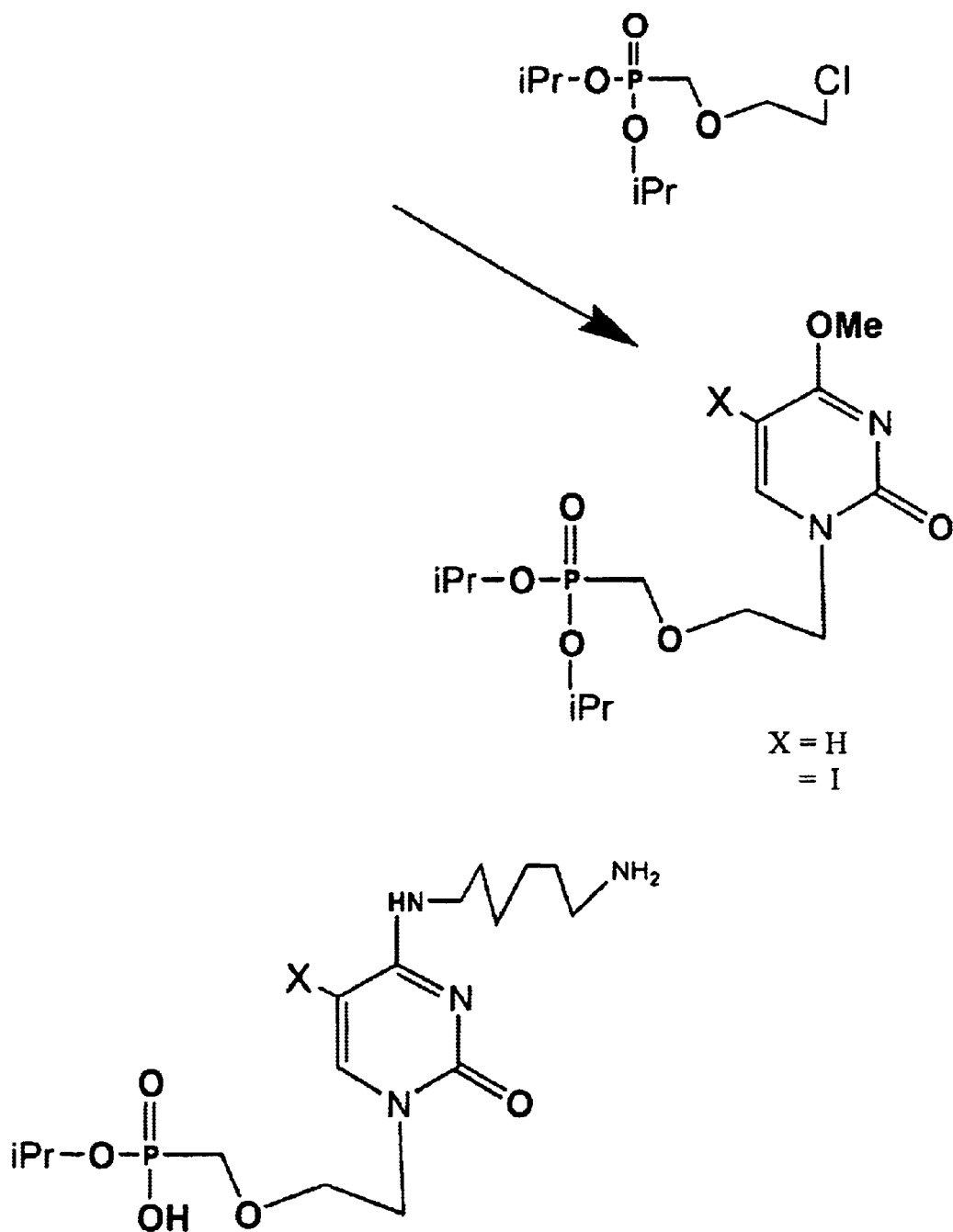
Figure 5C:
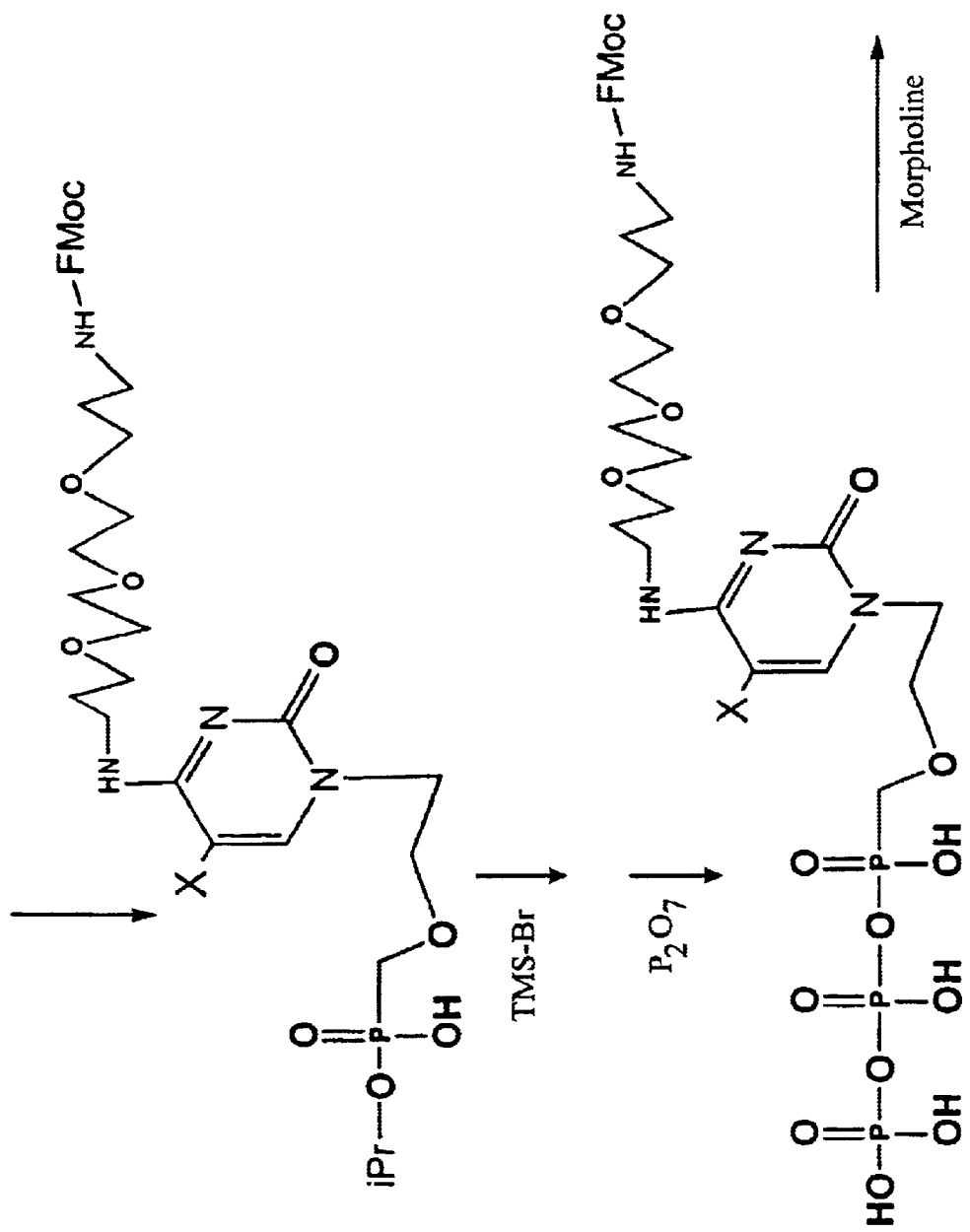
Figure 5D:
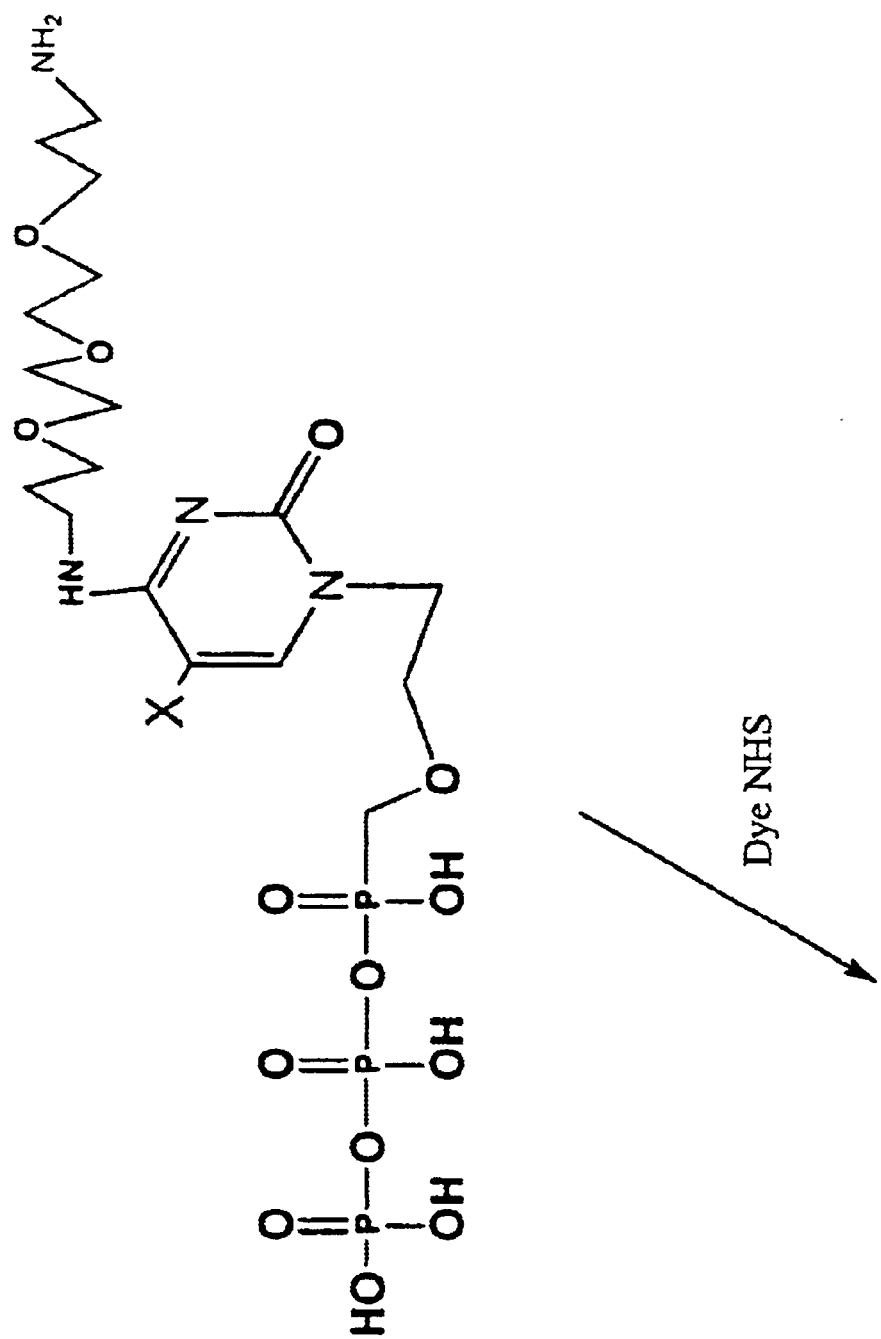
Figure 5E:
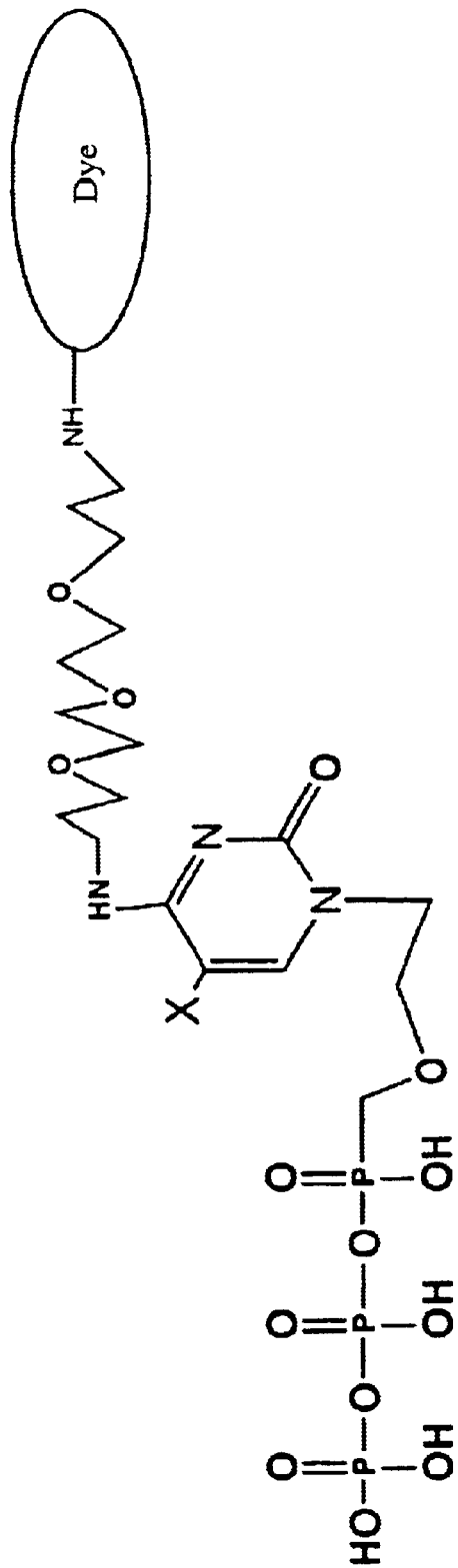

FIGS. 2 and 3 show examples of detectably labeled PME nucleotide analogs with various representative linkers. Linkers can comprise, for example, an alkyl, allyl, or alkynyl amine modifying group attached to the nucleobase (see e.g., FIG. 2, C-5-alkynyl-Fluor-PME-T, C-8-alkenyl-Fluor-PME-G and C-3-alkynyl-Fluor-PME-pyrazolo[3,4-d] pyrimidin-4-one). As an alternative, linkers can comprise one or more ethylene oxy moieties (see, e.g., FIG. 2, N6-Fluor-PME-A and N4-Fluor-PME-C). The linkers also include any chemical linking moieties located between the fluorescent dye and the reactive functionality (e.g., NHS group) attached to the dye before reaction with the nucleobase or intermediate linker.

The following figures depict the general chemical structure of linkers useful according to the invention. The figures and examples are meant to be exemplary; many additional structures known to those skilled in the art can serve the equivalent purpose of attaching a detectable marker, e.g., a fluorophore, to a nucleotide analog according to the invention.

Schematic structures for A and C analogs useful according to the invention are shown below:

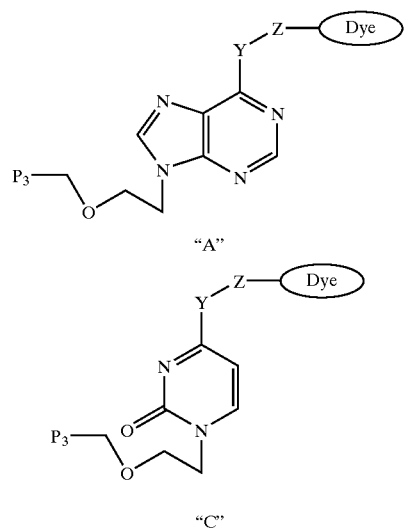

The linker "Y" on the A and C analogs can be described as follows. The most common linkers are essentially diamines connected to a carboxyl group on the dye, effecting an amide linkage. However, linkers can alternatively comprise S, O, or C reactive group termini, rather than N reactive group termini, on either or both ends of the linker moiety. The Z moiety is selected to be reactive with the group at the terminus of the linker that is not attached to the nucleobase. Thus, for example, when the terminus of linker Y that is not attached to the nucleobase is an amine, Z can represent a carboxyl moiety on the dye (or Z represents an additional linker plus a carboxyl moiety). Z can thus also be an amine, O, or S reactive group, as long as it is reactive with the free terminus of the selected linker Y.

Y can be selected, for example, from: hexanediamine, 4,7,10-trioxatriundecane-1,13-diamine, etc. or PEG-4-diamine. Alternatively, Y can be selected for example, from: —NH—(CH$_2$)$_3$—O—(CH$_2$)$_2$)—O—(CH$_2$)$_2$—O—(CH$_2$)$_3$ —NH—; —NH—(CH$_2$)$_n$—NH—, where n=2–8; —NH—(CH$_2$)$_2$—O—(CH$_2$)$_2$—O—(CH$_2$)$_2$—O—(CH$_2$)$_2$—NH—; and —NH—[(CH$_2$)$_2$—O—]$_n$—NH—, where n=2–6.

Alternatively, the linker can have a terminal carboxyl (and be attached to an amino group, Z, on the dye). Thus, linkers can be selected, for example, from: —NH—(CH$_2$)$_3$—O—(CH$_2$)$_2$)—O—(CH$_2$)$_2$—O—(CH$_2$)$_3$—C(O)—; —NH—(CH$_2$)$_n$—C(O)—, where n=2–8; —NH—(CH$_2$)$_2$—O—(CH$_2$)$_2$—O—(CH$_2$)$_2$—C(O)—; and —NH—[(CH$_2$)$_2$—O—]$_n$—C(O)—, where n=2–6.

A portion of the linker arm may also contain a carbocyclic (or heterocyclic) structure to effect rigidity. One example is a cyclohexyl component as described in Helvetica. Chim. Acta, 1999, 82: 1311–1323.

The linkers on the T and G analogs can be represented as follows:

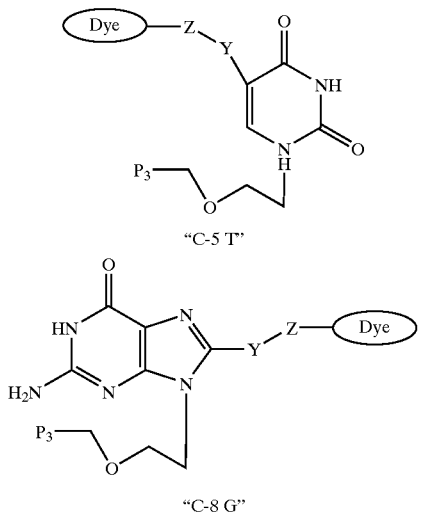

"C-5 T"

"C-8 G"

The linker "Y" on the T and G analogs can be described as follows. The dyes can be attached to the nucleobase via hydrocarbon linkers containing O, S, or N terminal atoms (e.g., J Med. Chem, 1980, 23: 569; Nucleosides, Nucleotides and Nucleic Acids, 1997, 16: 107–114) but are attached preferably through a carbon-carbon covalent bond, preferably containing a terminal alkyne or alkene functionality. (See, for example, U.S. Pat. Nos. 5,151,507, 5,608,063, 5,047,519, 5,093,232 and 5,476,928; Russian Chem. Rev. 1999, 68: 483–504; J. Chem. Soc. Chem. Commun. 1994: 1997–8, etc). Additional linkages are described in Nucl. Acids Res. 2001, 29: 1565–1573. The opposite end of the linker Y can have an amine, carboxyl, S or O-containing reactive group complementary to the reactive group Z on the dye. Thus, the two reactive termini of linker Y can be the same or different, as long as they are complementary to the reactive groups on the nucleobase and dye, respectively.

Z is as described above, and can be amino, carboxyl, or an O or S-containing group, as long as Z is a reactive group complementary to the free reactive group on the linker Y after Y is attached to the nucleobase.

Non-limiting examples of the linker Y include:
a) linkers attached through N:
—NH—$(CH_2)_3$—O—$(CH_2)_2$—O—$(CH_2)_2$—O—$(CH_2)_3$—NH—; —NH—$(CH_2)_n$—NH—, where n=2–8; —NH—$(CH_2)_2$—O—$(CH_2)_2$—O—$(CH_2)_2$—O—$(CH_2)_2$—O—$(CH_2)_2$—NH—; and —NH—$[(CH_2)_2$—O$]_n$—NH—, where n=2–6.
b) linkers attached through O:
—O—$(CH_2)_3$—O—$(CH_2)_2$—O—$(CH_2)_2$—O—$(CH_2)_3$—NH—; —O—$(CH_2)_n$—NH—, where n=2–8; —O—$(CH_2)_2$—O—$(CH_2)_2$—O—$(CH_2)_2$—O—$(CH_2)_2$—O—$(CH_2)_2$—NH—; and —O—$[(CH_2)_2$—O$]_n$—NH—, where n=2–6.
c) linkers attached through S:
—S—$(CH_2)_3$—O—$(CH_2)_2$—O—$(CH_2)_2$—O—$(CH_2)_3$—NH—; —S—$(CH_2)_n$—NH—, where n=2–8; —S—$(CH_2)_2$—O—$(CH_2)_2$—O—$(CH_2)_2$—O—$(CH_2)_2$—O—$(CH_2)_2$—NH—; and —S—$[(CH_2)_2$—O$]_n$—NH—, where n=2–6.
d) linkers attached through C:
—$(CH_2)_n$—NH—, n=2–15; —C=C—C(O)—$(CH_2)_n$—NH—; n=2–8; —$(CH_2)_n$—Q—, n=2–15 or —C=C—C(O)—Q—, where Q is selected from —NH—$(CH_2)_3$—O—$(CH_2)_2$—O—$(CH_2)_2$—O—$(CH_2)_3$—NH—, —NH—$(CH_2)_n$—NH— (where n=2–12), —NH—$(CH_2)_2$—O—$(CH_2)_2$—O—$(CH_2)_2$—O—$(CH_2)_2$—NH—, —NH—$[(CH_2)_2$—O$]_n$—NH— (where n=2–6), —$(CH_2)_n$—NH— (where n=2–8), —$(CH_2)_3$—O—$(CH_2)_2$—O—$(CH_2)_2$—O—$(CH_2)_3$—NH—, —$(CH_2)_n$—NH— (where n=2–8), —$(CH_2)_2$—O—$(CH_2)_2$—O—$(CH_2)_2$—O—$(CH_2)_2$—O $(CH_2)_2$—NH—, and —$[(CH_2)_2$—O$]_n$—NH— (where n=2–6).

Alternatively, the linker can have a terminal carboxyl (and be attached to an amino group, Z, on the dye). Thus, the linker can be, for example: —NH—$(CH_2)_3$—O—$(CH_2)_2$—O—$(CH_2)_2$—O—$(CH_2)_3$—C(O)—; —NH—$(CH_2)_n$—C(O)—, where n=2–8; —NH—$(CH_2)_2$—O—$(CH_2)_2$—O—$(CH_2)_2$—O—$(CH_2)_2$—O $(CH_2)_2$—C(O)—; and —NH—$[(CH_2)_2$—O$]_n$—C(O)—, where n=2–6. Attachment to the dye can be through an oximino (Nucleosides, Nucleotides & Nucleic Acids 1999, 18: 979–980).

Preferably Y is selected from: —C=C—C(O)—$(CH_2)_n$—NH—, n=2–8; —C=C—C(O)—NH—$(CH_2)_n$—NH—, n=2–8; and —C=C—$(CH_2)_n$—Q— (where n=2–8), —C≡C—$(CH_2)_n$—Q— (where n=2–8), or —C≡C—C(O)—Q—, where Q is selected from —NH—$(CH_2)_3$—O—$(CH_2)_2$—O—$(CH_2)_2$—O—$(CH_2)_3$—NH—, —NH—$(CH_2)_n$—NH— (where n=2–12), —NH—$(CH_2)_2$—O—$(CH_2)_2$—O—$(CH_2)_2$—O—$(CH_2)_2$—O $(CH_2)_2$—NH—, —NH—$[(CH_2)_2$—O$]_n$—NH— (where n=2–6), —$(CH_2)_n$—NH— (where n=2–8), —$(CH_2)_3$—O—$(CH_2)_2$—O—$(CH_2)_2$—O—$(CH_2)_3$—NH—, —$(CH_2)_n$—NH— (where n=2–8), —$(CH_2)_2$—O—$(CH_2)_2$—O—$(CH_2)_2$—O—$(CH_2)_2$—O $(CH_2)_2$—NH—, and —$[(CH_2)_2$—O$]_n$—NH— (where n=2–6).

A portion of the linker arm can also contain a carbocyclic (or heterocyclic) structure to effect rigidity. One example is a cyclohexyl component as described in Helvetica. Chim. Acta, 1999, 82: 1311–1323.

Attachment to a fluorescent dye (or other detectable marker) can be through an oximino (Nucleosides, Nucleotides & Nucleic Acids 1999, 18: 979–980). Alternatively, the linker can have a terminal carboxyl (and be attached to an amino group, Z, on the dye). The following are non-limiting examples of this arrangement: —NH—$(CH_2)_3$—O—$(CH_2)_2$—O—$(CH_2)_2$—O—$(CH_2)_3$—C(O)—, —NH—$(CH_2)_n$—C(O)— n=2–8, also —NH—$(CH_2)_2$—O—$(CH_2)_2$—O—$(CH_2)_2$—O—$(CH_2)_2$—O $(CH_2)_2$—C(O)—, —NH—$[(CH_2)_2$—O$]_n$—C(O)— n=2–6; other linkers described herein above or known in the art can also comprise a terminal carboxyl for the same purpose.

The effects of linkers attached to deoxyuridine (dU) residues on oligonucleotide hybidization is described in Bull. Chem. Soc. Jpn 1995, 68: 1981–1987. The effects described provide guidance to one skilled in the art regarding the design and placement of linkers onto dU residues such that they continue to permit oligonucleotide hybridization.

Linkers on alternative T and G analogs:

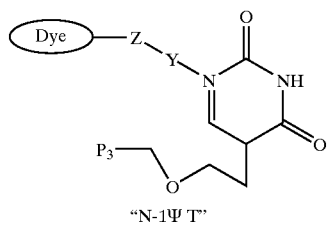

"N-1Ψ T"

-continued

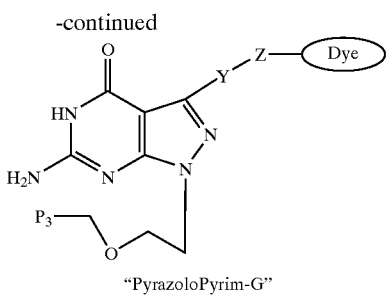

"PyrazoloPyrim-G"

Z is as described above.

For the "Pyrazolopyrim G" analog, Y is as described for the T and G analogs, above.

For the "N-1-ψT" analog, Y can be selected from: —(CH$_2$)$_n$—NH—, n=2–15; —C—C—C(O)—(CH$_2$)$_n$—NH—, n=2–8; and —(CH$_2$)$_n$—Q— (where n=2–15) or —C—C—C(O)—Q—, where Q is selected from —NH—(CH$_2$)$_3$—O—(CH$_2$)$_2$—O—(CH$_2$)$_2$—O—(CH$_2$)$_3$—NH—, —NH—(CH$_2$)$_n$—NH— (where n=2–12), —NH—(CH$_2$)$_2$—O—(CH$_2$)$_2$—O—(CH$_2$)$_2$—O (CH$_2$)$_2$—NH—, —NH—[(CH$_2$)$_2$—O]$_n$—NH— (where n=2–6), —(CH$_2$)$_n$—NH— (where n=2–8), —(CH$_2$)$_3$—O—(CH$_2$)$_2$—O—(CH$_2$)$_2$—O—(CH$_2$)$_3$—NH—, —(CH$_2$)$_n$—NH— (where n=2–8), —(CH$_2$)$_2$ —O—(CH$_2$)$_2$—O—(CH$_2$)$_2$—O—(CH$_2$)$_2$—O (CH$_2$)$_2$—NH—, and —[(CH$_2$)$_2$—O]$_n$—NH— (where n=2–6).

Synthesis of PME Nucleotide Analogs

PME nucleotide analogs useful according to the invention can be synthesized using methods known in the art or described herein. The synthesis of PME-A is described by Holy & Rosenberg, 1987, Collect. Czech. Chem. Commun. 52: 2775, Holy & Rosenberg, 1987, Collect. Czech. Chem. Commun. 52: 2801, Holy et al., 1990, supra, and Starrett et al., 1994, J. Med. Chem. 37: 1857–1864, each of which is incorporated herein by reference. The general synthesis of nucleoside 5'-triphosphates is described by Moffatt, 1964, Can. J. Chem. 42: 599, which is also incorporated herein by reference.

The PME nucleoside analogs can be made using precursors and synthetic pathways known in the art. For example, the precursor 2-chloroethoxymethyl chloride was made following J. Heterocycl. Chem., 2000, 37: 1187–91 and converted to diethy-2-chloroethoxymethylphosphonate as described (Collect. Czech. Chem. Commun. 1989, 54: 2190), or converted to di-(2-propyl)-2-chloroethoxymethylphosphonate as described in J. Heterocycl. Chem., 2000, 37: 1187–91. Alkylations (attachment of the nucleobases) are performed according to the general procedures described in J. Med. Chem. 1999, 42: 2064–2086.

Fluorescently Labeled PME-A-pp Analog:

The synthesis of a fluorescently-labeled PME-A nucleotide analog is described below. The synthetic scheme is shown schematically in FIG. 4.

Di-(2-propyl)-2-chloroethoxymethylphosphonate is reacted with 6-chloropurine in the presence of sodium hydride to effect attachment at the N-9 position as described (J. Med. Chem. 1999, 42: 2064–2086). Either of two routes can then be followed. Preferably, (Route A) diester hydrolysis is effected using bromotrimethylsilane. Pyrophosphorylation according to the procedure of Moffat (Can.J. Chem. 1964, 42, 599—specifically described in Collect. Czech. Chem. Commun. 1987, 52, 2801–9), to yield the diphosphate derivative (triphosphate analog). Displacement of the 6-chloro group with 4,7,10-trioxatriundecane-1,13-diamine provides the requisite linker attachment to the purine base. Coupling of the dye is then accomplished in aqueous sodium borate buffer using an activated ester (N-hydroxysuccinimide) derivative of the fluorescent dye to give the desired fluorescently labeled PME-A-pp Analog.

Route B, which can be followed if the 6-chlor group proves too labile in the pyrophosphorylation procedure, is as follows. After monoester hydrolysis of the phosphonate group, the 6-chloro group is displaced with 4,7,10-trioxatriundecane-1,13-diamine and the amine terminus is blocked by reaction with Fmoc succinimidyl ester. The remaining phosphate ester is then deprotected using bromotrimethylsilane. Pyrophosphorylation can then be performed as described in Route A, followed by deprotection of the Fmoc functionality using aqueous morpholine. Coupling of the dye as described in Route A will then yield the desired fluorescently labeled PME-A-pp Analog.

Fluorescently Labeled PME-C-pp Analog:

The synthesis of a fluorescently-labeled PME-C nucleotide analog is described below. The synthetic scheme is shown schematically in FIG. 5.

4-Methoxy pyrimidin-2-one is synthesized as described (Nucl. Acids. Res. 1973: 19–34), or by a more straightforward route (e.g., that taught in U.S. Pat. No. 5,359,067) from uracil via its 4-(1,2,4-triazolide) derivative. Reaction with di-(2-propyl)-2-chloroethoxymethylphosphonate effects alkylation an the N-1 position of the pyrimidine ring as described (Collect. Czech. Chem. Commun. 1989, 54: 2190–2209). Following monoester hydrolysis of the phosphonate group using lithium azide, the 4-methoxy group is displaced with 4,7,10-trioxatriundecane-1,13-diamine and the amine terminus is subsequently blocked by reaction with Fmoc succinimidyl ester. The remaining phosphate ester is then deprotected using bromotrimethylsilane. Pyrophosphorylation, deprotection and dye coupling are then performed as described above (in the synthesis of the PME-A analog) to yield the fluorescently labeled PME-C-pp analog.

Figure 6:
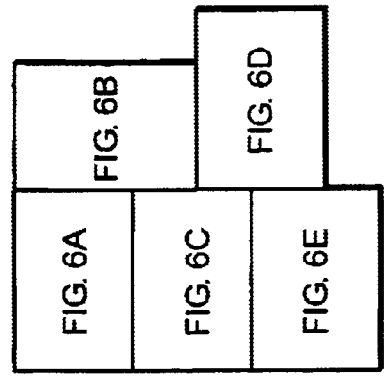
FIG. 6 schematically shows steps in a synthesis pathway for PME-Tpp nucleotide analog.
Figure 6A:
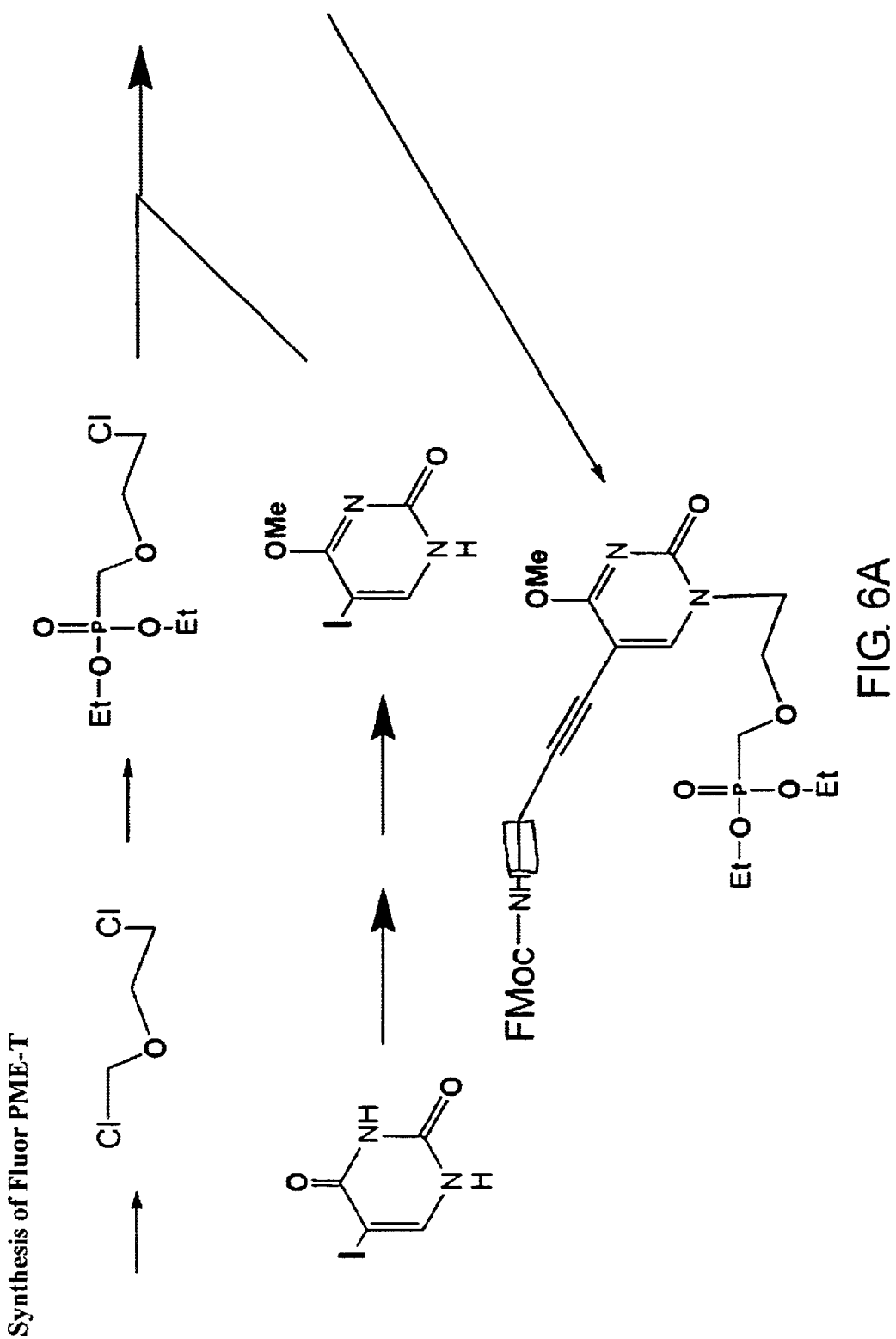
Figure 6B:
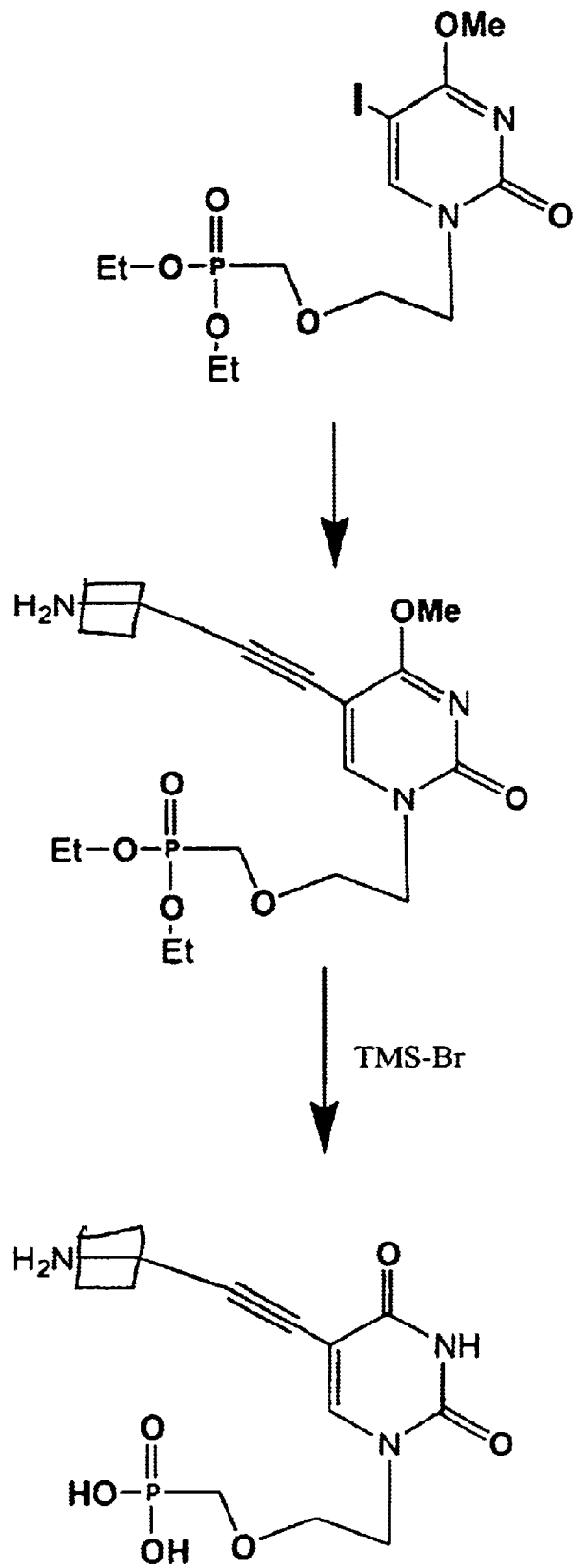
Figure 6C:
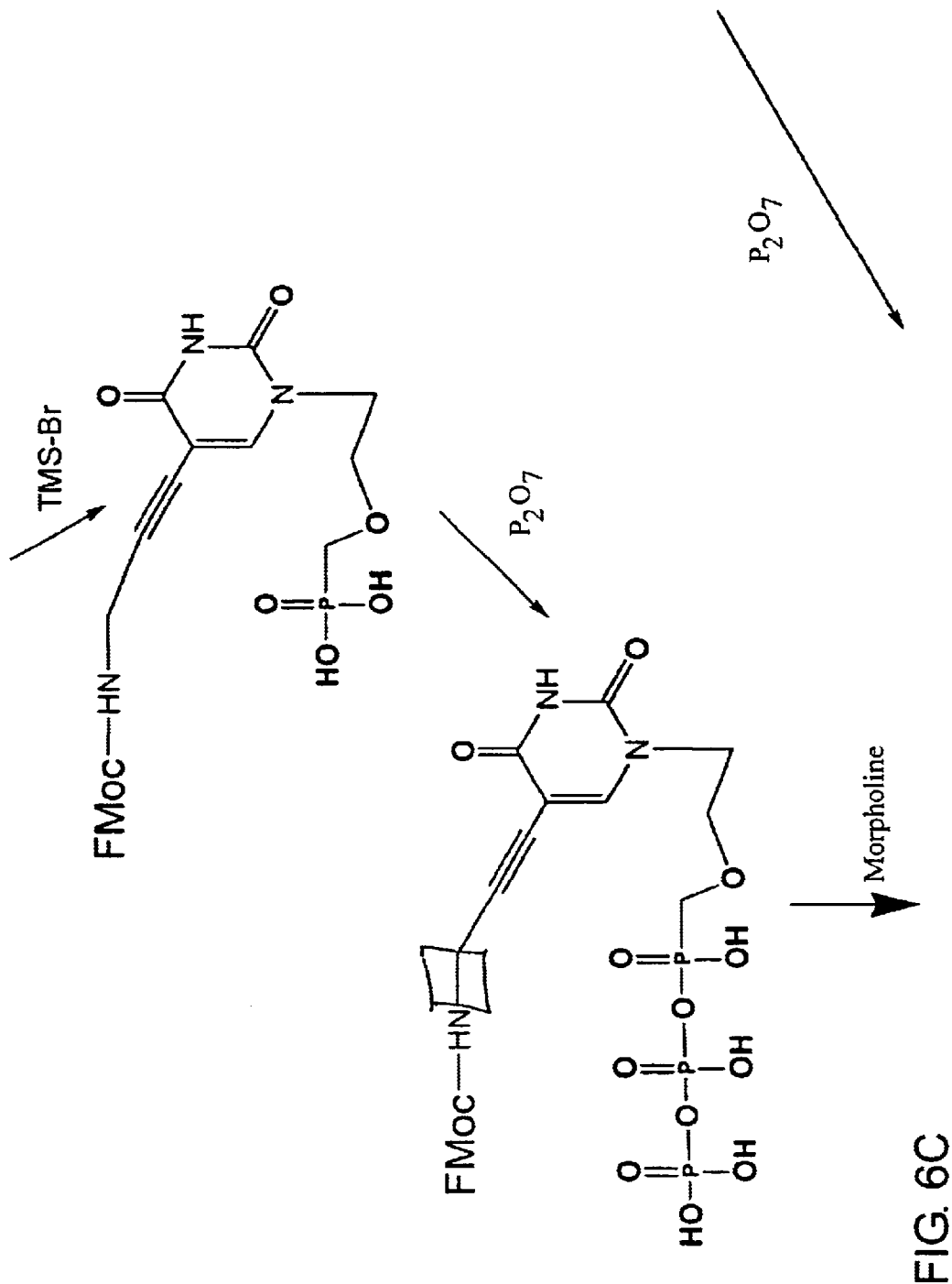
Figure 6D:
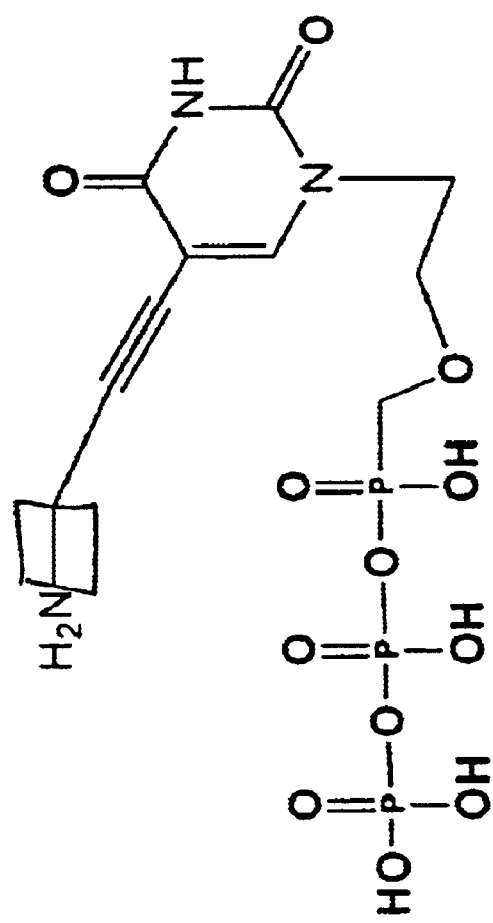
Figure 6E:
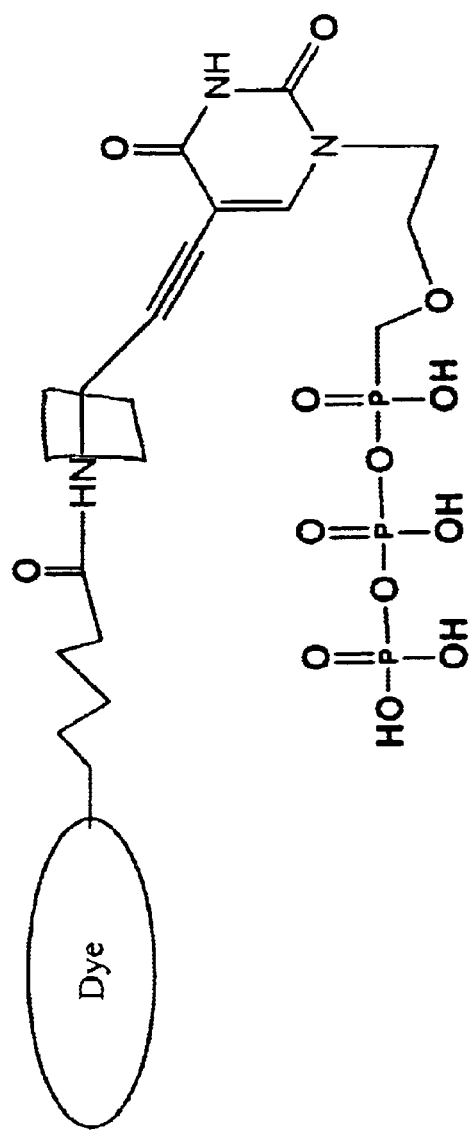

Fluorescently Labeled PME-T-pp Analog:

The synthesis of a fluorescently-labeled PME-T nucleotide analog is described below. The synthetic scheme is shown schematically in FIG. 6.

5-Iodo-4-methoxy pyrimidin-2-one iss synthesized starting with 5-iodouracil. Alkylation with di-(2-propyl)-2-chloroethoxymethylphosphonate is then accomplished as described for the PME-C analog, above. Reaction of N-1-phosphonmethoxyethyl-5-iodo-4-methoxy pyrimidin-2-one- with Fmoc-protected propargylamine in the presence of a palladium(0) catalyst (J. Org. Chem. 1989: 54, 3420–3422) provides for attachment of a propargylamine linker at the pyrimidine C-5 position. Reaction with bromotrimethylsilane effects ether cleavage of the 4-methoxy group and concomitant phosphonate diester hydrolysis to give the Fmoc-protected propargylamine derivative of PME-T. Pyrophosphorylation, deprotection and dye coupling are then accomplished as described above (in the synthesis of the PME-A analog) to yield the fluorescently labeled PME-T-pp analog.

Figure 7:
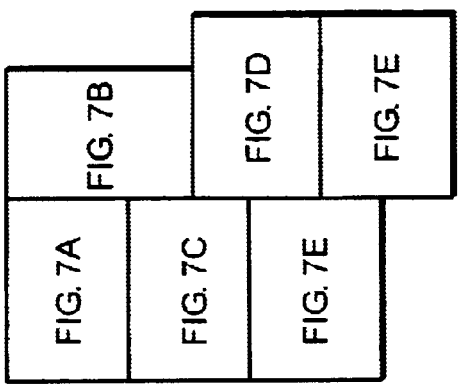
FIG. 7 schematically shows steps in a synthesis pathway for PME-Gpp nucleotide analog (Pyrazolo[3,4-d]pyrimidine nucleotide analog).
Figure 7B:
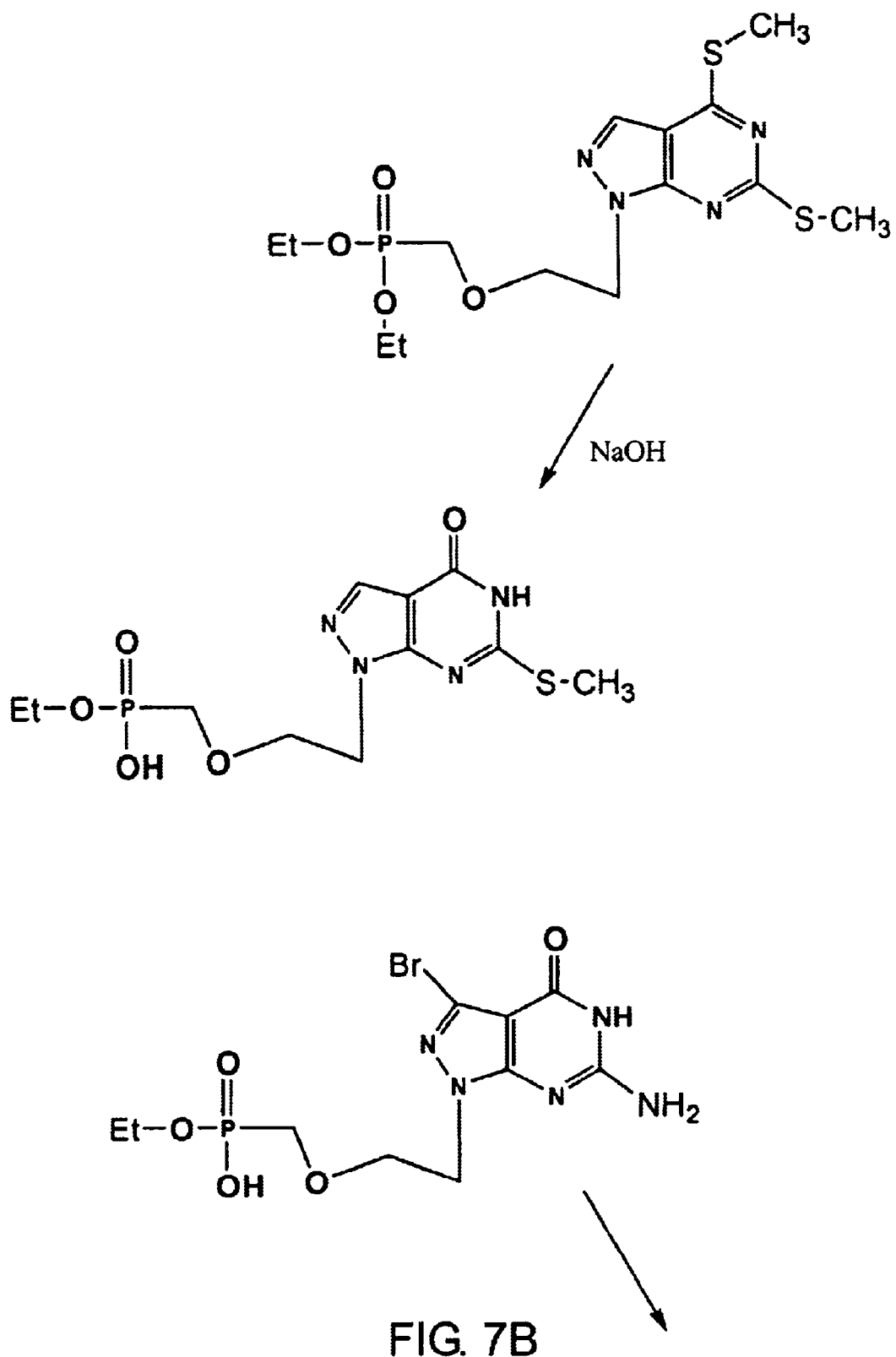
Figure 7C:
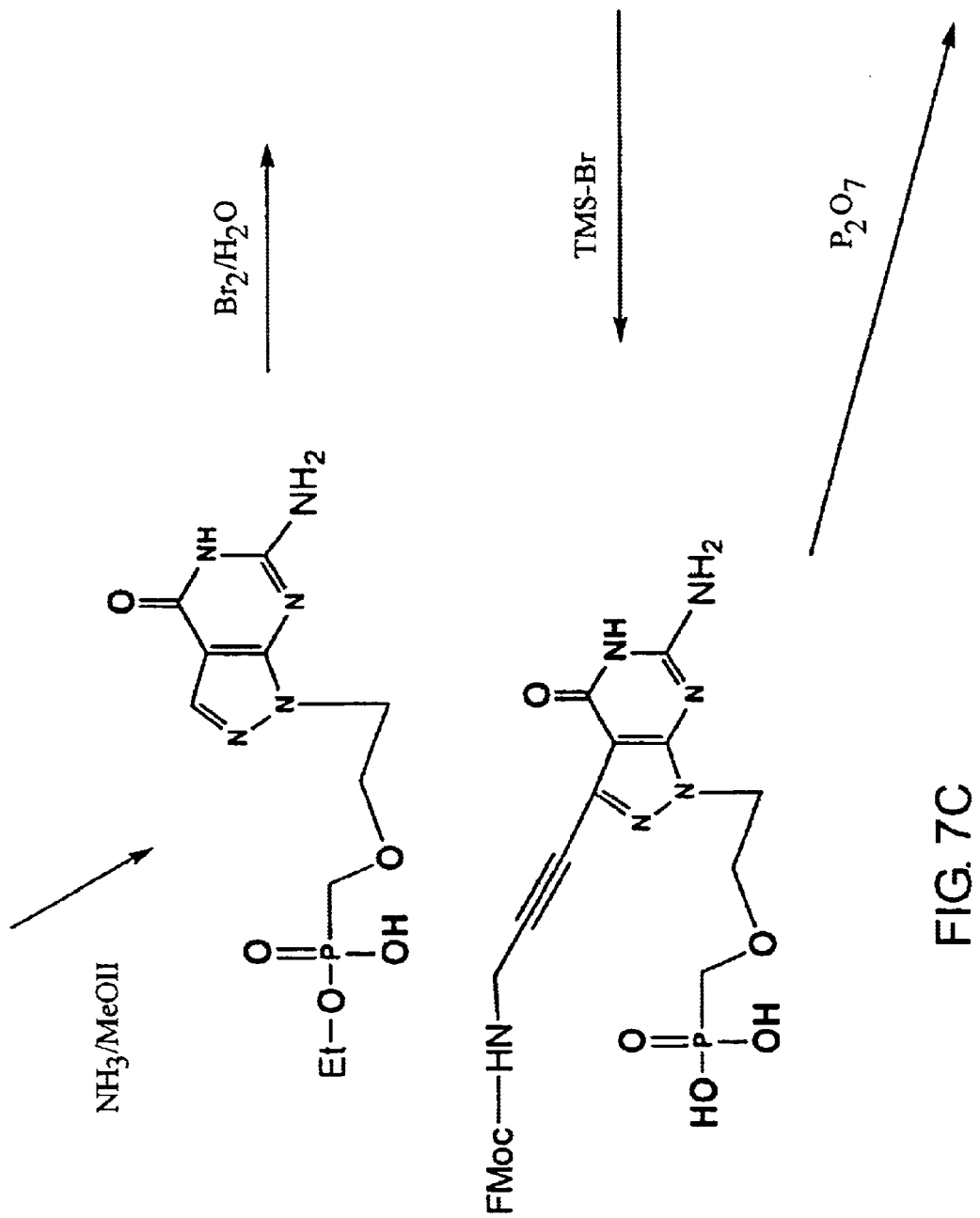
Figure 7D:
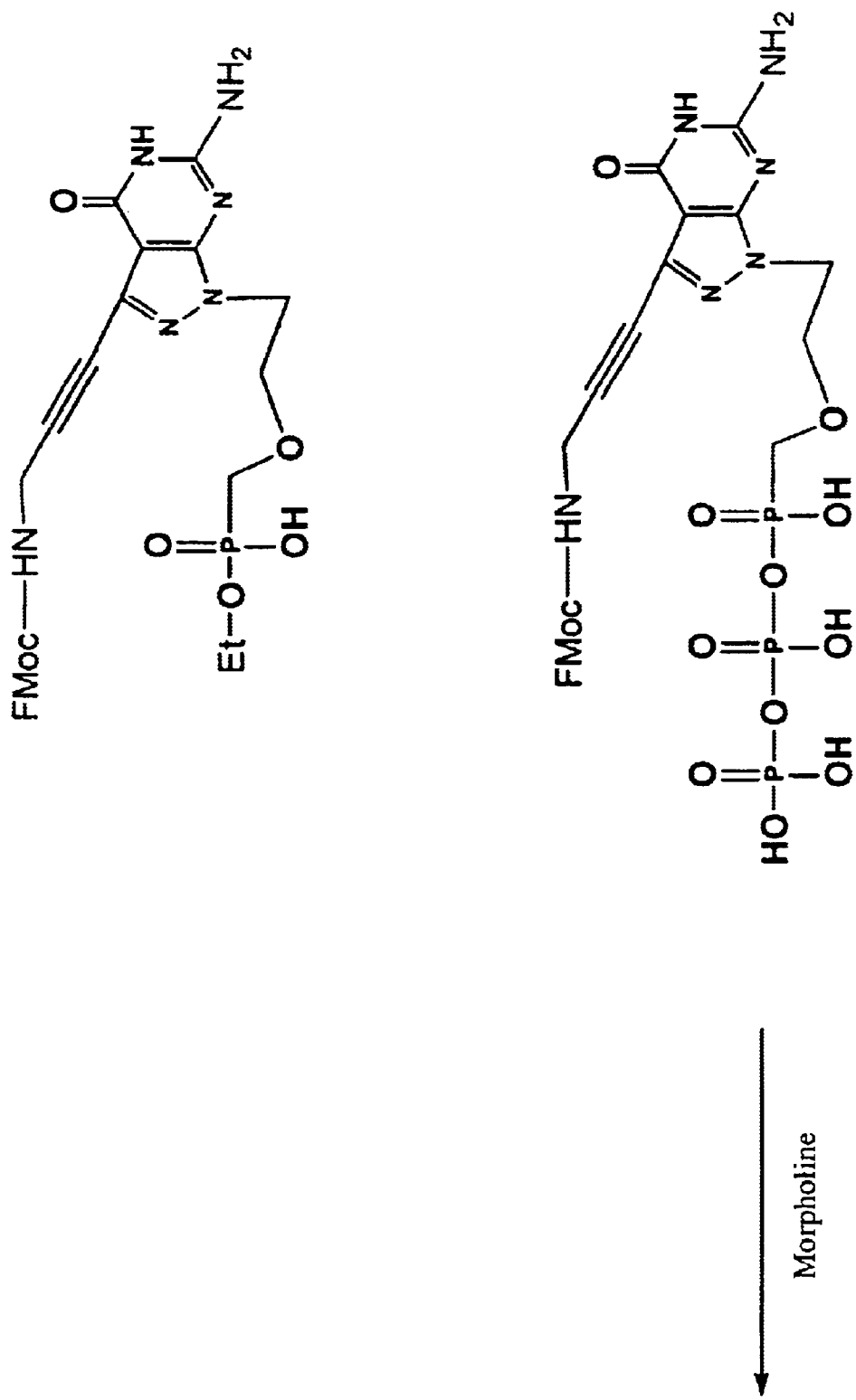
Figure 7E:
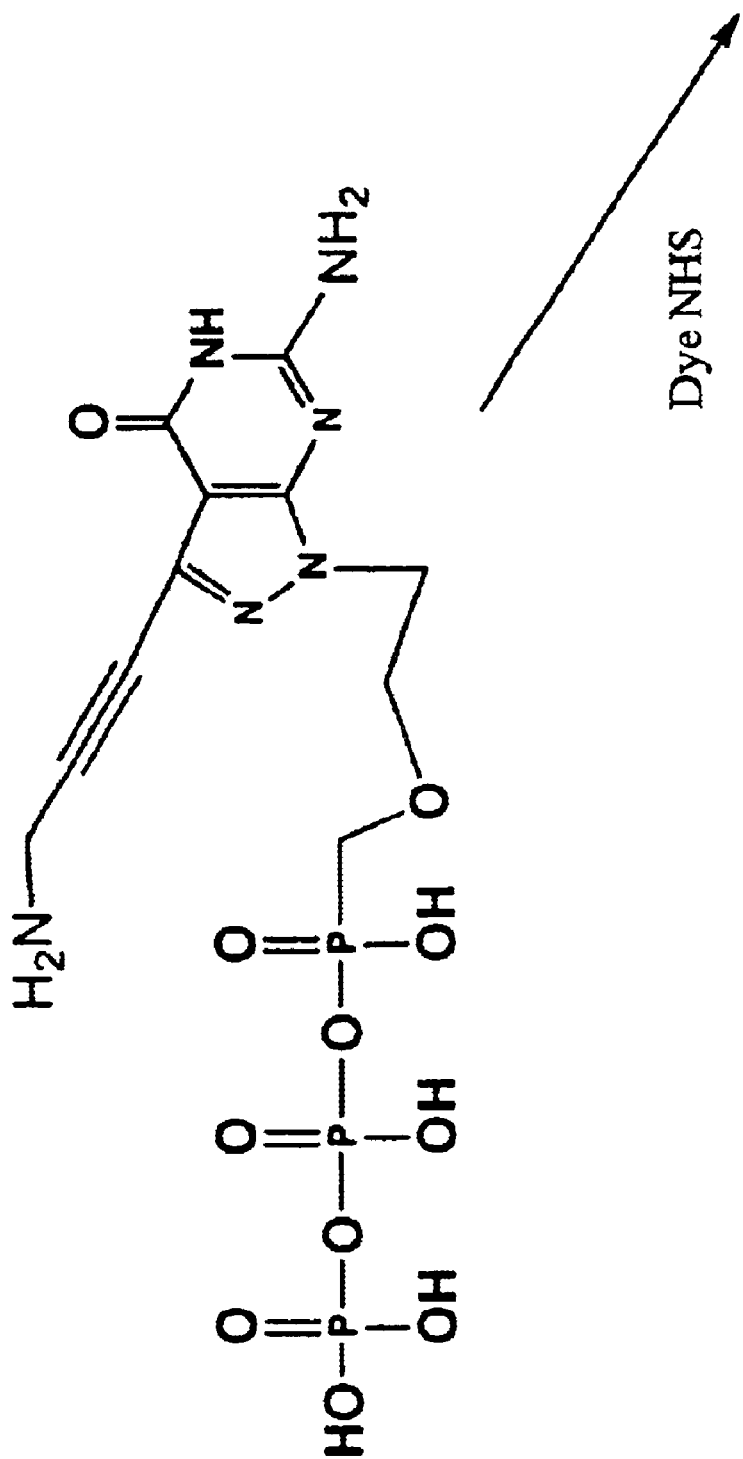
Figure 7F:
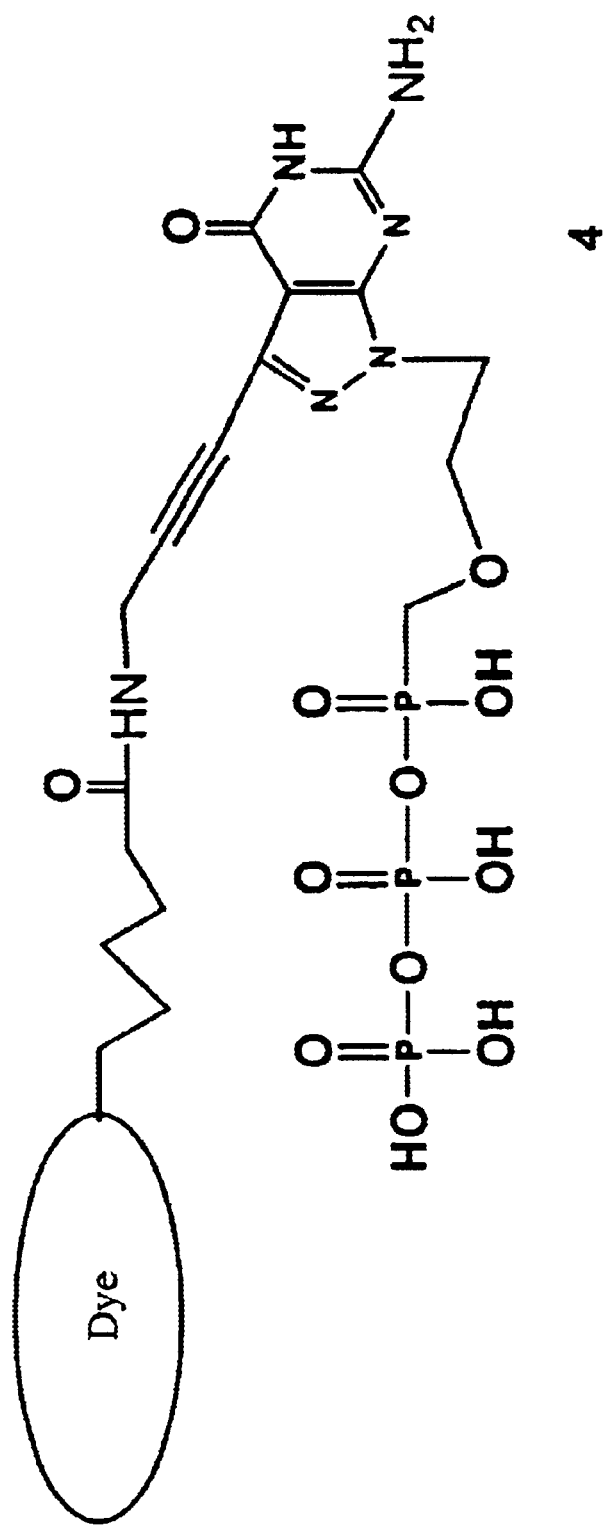

Fluorescently Labeled PME-G-pp Analog (Pyrazolo[3,4-d]pyrimidine analog):

The synthesis of a fluorescently-labeled PME-Gpp nucleotide analog is described below. The synthetic scheme is shown schematically in FIG. 7.

Di-(2-propyl)-2-chloroethoxymethylphosphonate is reacted with 4,6-bismethylmercapto-pyrazolo[3,4-d] pyrimidine (Tetrahedron, 1967, 23: 891) in the presence of DBU to effect attachment at the pyrazole ring nitrogen(s).

Displacement of the 4-methymercapto functionality and concomitant monoester hydrolysis is then effected using aqueous sodium hydroxide. Displacement of the remaining 6-methymercapto group is accomplished (after initial oxidation with m-chloroperbenzoic acid to the intermediate methy sulfone) using methanolic ammonia. Bromination at the 3-position is performed according to the procedure described in J. Med. Chem. 1984, 27: 1026–30. Displacement of the 3-bromo group with Fmoc-protected propargylamine is effected using the palladium(0) catalyst described above. The remaining phosphate ester is then deprotected using bromotrimethylsilane. Pyrophosphorylation, deprotection and dye coupling are then performed as described above to yield the fluorescently labeled PME-G-pp analog (pyrazolo[3,4-d]pyrimidine analog).

Labeling of PME Nucleotide Analogs

PME nucleotide analogs can be labeled in any of a variety of ways known to those skilled in the art. While radiolabels and fluorescent labels are preferred, PME nucleotide analogs according to the invention can also, for example, be tagged with an affinity label (e.g., biotin, iminobiotin) or enzyme substrate, or tagged with an epitope tag or enzyme.

Preferred radiolabels include, but are not limited to $^{35}$S, $^{32}$P or $^{33}$P. For $^{32}$P or $^{33}$P labeling, it is preferred that the labels be added by replacement of the phosphorus in the phosphonomethoxy group with the isotope. For $^{35}$S labeling, it is preferred that the oxygen of the phosphonate group be replaced with the $^{35}$S (i.e., the $^{35}$S is covalently linked to the P of the phosphonate group). Such radiolabeling is performed according to methods known to thise skilled in the art. Alternatively, a radiolabel may be appended to the PME nucleotide via a linker attached to the nucleobase (see below).

Any fluorescent label known to be useful for nucleic acid labeling is specifically contemplated to be useful as a label according to the invention. A great many fluorescent dyes in various forms amenable to labeling reactions are commercially available, from, for example, Molecular Probes (Eugene, Oreg.) or Sigma (St Louis, Mo.). Preferred fluorescent dyes include, but are not limited to Cy5, Cy3, TAMRA, R6G, R110, ROX, JOE, FAM, Texas Red™, and Oregon Green™, each of which is widely available commercially. Other dyes useful according to the invention include, but are not limited to squaraine dyes (e.g., as reported by Lakowicz, J. R., et al., 1994, Anal. Biochem. 217: 197–204), oxonols (e.g., as reported by Waggoner, A. S., et al, 1995, J. Fluorescence 5: 231–235), Dibenzazoles (Brown, L R, WO99/03849, Appl, # PCT/US98/15080), dyes absorbing in the near-IR region (e.g., as described by Patonay, G., 1992, J. Org. Chem. 57: 4578–4580 and U.S. Pat. No. 5,800,995), near-IR heavy atom dyes (Soper, S. A., 1998, Anal Chem., 70: 2676–2684) rhodamine dyes exhibiting variable fluorescent lifetimes (as described by Drexhage, et al, 1995, J. Fluorescence, 5: 247–260 and ibid, 1993, 3: 131–139), dichlororhodamine dyes (U.S. Pat. No. 5,847,162) and aromatic-substituted xanthene dyes (U.S. Pat. No. 6,008,379).

For some nucleic acid sequencing applications, it is advantageous to use a set of two or more (often four) spectrally distinguishable fluorescently labeled PME nucleotide analogs. The use of such sets permits sequencing reactions to be run in a single tube or reaction vessel and to be electrophoresed in a single lane of a gel, thereby increasing the throughput of the process. Alternatively, if the reactions are being performed on an array, the use of four spectrally distinguishable fluorophores will also speed the sequencing process, because, for example, all four terminators can be included in a single extension reaction on the array, followed by a single detection step, rather than requiring the addition of each terminator in turn, with washing and detection steps after each terminator. One example of a spectrally distinguishable set of fluorescent dyes comprises rhodamine 6G (R6G), tetramethyl rhodamine (TAMRA), rhodamine 110 (R110), and rhodamine X (ROX), which are available in a number of forms (including NHS esters), from, for example, Molecular Probes (Eugene, Oreg.). Another set of spectrally distinguishable dyes used in fluorescent sequencing operations is FAM, JOE, TAMRA, and ROX, also available from Molecular Probes. Other sets of spectrally distinguishable fluorescent dyes useful according to the invention are commonly used in commercially-available dye-terminator sequencing kits (e.g., the ABI Terminator Cycle Sequencing Kit) and can be readily assembled by those of skill in the art.

Fluorescent labels, as well as, for example, radiolabels, affinity tags or enzyme substrates are preferably attached to the PME nucleotide analog via a linker attached to the nucleobase. Because linkers put distance between the label and the nucleobase, the linker is less likely to interfere with polymerase enzyme recognition and activity or with complementary hydrogen bond formation between the analog's nucleobase and that on an adjacent template nucleotide.

Nucleic Acid Sequencing:

Nucleic acid sequencing methods are widely known in the art. Methods of particular importance to the invention are those based upon the enzymatic incorporation of a chain terminator into the growing polynucleotide chain. The original chain terminator method was described by Sanger, et al. (1977, Proc. Natl. Acad. Sci. U.S.A., 74: 5463–5467). In this method, a single-stranded template nucleic acid is sequenced by using a nucleic acid polymerase to synthesize a set of polynucleotide fragments wherein the fragments (a) have a sequence complementary to the template nucleic acid sequence, (b) differ in length by a single nucleotide, and (c) have a 5'-end terminating in a known nucleotide, e.g., A, C, G, or T. In the Sanger method, an oligonucleotide primer is hybridized to the template nucleic acid, and the 3'-end of the primer serves as an initiation site for polymerase-mediated polymerization of a complementary polynucleotide fragment. The primer extension reaction comprises contacting the annealed template-primer hybrid with the four deoxynucleotides (dA, dC, dG and dT), a nucleic acid polymerase enzyme, and one nucleotide chain terminator (Sanger's method called for 2',3'-dideoxynucleotide triphosphate chain terminators). The incorporation of the dideoxy terminator forms a primer extension product which lacks a hydroxy group at the 3'-terminus and thus can not be further extended by the polymerase. Four separate primer extension reactions are performed, each including a single terminator corresponding to one of dA, dC, dG and dT. The competition between the dNTP and its corresponding terminator for incorporation by the polymerase results in a distribution of different-sized extension products, each extension product terminating with the particular terminator used in the reaction. Electrophoretic separation of the four separate reactions in parallel produces a "ladder" of extension fragments, each starting with the annealed primer common to all reactions and ending with one of the four terminators used. The sequence of the complement (and thereby the sequence of the template) is read directly from the order of fragments on the gel.

Numerous variations on the Sanger method are known to those skilled in the art. The fragments generated in the sequencing reactions were originally detected through use of radiolabel ($^{32}$P or $^{35}$S) incorporated either into the primer or into one of the dNTPs. More recently, detection has been achieved by labeling each terminator with a fluorescent dye (see e.g., Prober et al., Science, 238: 336–341 (1987); and U.S. Pat. No. 5,151,507). The use of fluorescent dyes overcomes problems related to the limited shelf life of radiolabeled products and the difficulties in handling, storing and disposing of radioactive wastes generated in the process. As noted above, the use of four spectrally distinguishable fluorescent dyes, one on each terminator, also permits the sequencing reaction to be performed in a single tube or vessel, instead of the four tubes necessary for the original method.

Other variations on the Sanger process include the use of thermostable nucleic acid polymerase enzymes, and "cycle sequencing", which is essentially a PCR reaction performed in the presence of a chain terminator. Among other advantages, thermostable polymerases and cycle sequencing increase the sensitivity of the reactions by reducing the amount of starting template needed and overcome the need for single-stranded template molecules.

PME nucleotide analog chain terminators according to the invention can be used in a sequencing or minisequencing protocol in place of dideoxynucleotide chain terminators commonly used in the art. PME nucleotide chain terminators according to the invention have the advantage of lower cost relative to dideoxynucleotide triphosphates. Given the growing importance of sequencing technology, even a minor cost savings per nucleotide base would translate to very large dollar value savings when multiplied times the number of bases being sequenced.

Nucleic acid sequencing methods using the PME nucleotide analogs according to the invention will generally have the scheme where an oligonucleotide primer is annealed to a sequencing template polynucleotide, and the annealed primer/template complex is contacted with a nucleic acid polymerase enzyme in the presence of a PME nucleotide analog, under conditions and for a time sufficient to permit extension of the primer by the polymerase. Incorporation of the PME nucleotide analog under these conditions permits the determination of nucleic acid sequence information about the template polynucleotide because the analog is only incorporated where it is the complement of a template nucleotide. Incorporation is generally detected following size separation of the extension products, but can also be measured without such size separation, as in the minisequencing methods (see below). Reactions will most often include deoxynucleotide triphosphates in addition to one or more PME nucleotide analog chain terminators, but variations such as the minisequencing methods do not necessarily require this.

As noted above, the so called "minisequencing" techniques also benefit from the PME nucleotide analogs according to the invention. Minisequencing generates limited sequence information, most often information about a single nucleotide. Minisequencing techniques have become increasingly important as researchers and clinicians seek to determine the genotypes of individuals with respect to polymorphisms and mutations (see, e.g., Syvanen et al., 1990, Genomics, 8:684–692; Makridakis & Reichardt, 2001, Biotechniques 6:1374–1380). There are numerous variations on the technique, but the basic premise is that a primer is annealed so that its 3' end is hybridized to the template nucleotide immediately adjacent to the nucleotide one wishes to identify. The annealed template is then exposed to a nucleic acid polymerase (e.g., Taq polymerase) and a labeled chain terminator nucleotide triphosphate analog, followed by detection of incorporated label. If the analog is incorporated by the polymerase enzyme, the unknown nucleotide is identified as the complement of the nucleobase of the analog. If the analog is not incorporated, the process is repeated with chain terminator analogs for each of the three remaining nucleotide triphosphates until one is incorporated, thereby identifying the template nucleotide. In one important variation, four different fluorescently labeled chain terminator analogs are included in the same reaction, one corresponding to each of dA, dC, dG and dT, followed by detection of incorporated fluorescence. If the four analogs are labeled with spectrally distinguishable fluorophores, the identity of the target nucleotide can be identified from a single reaction.

The minisequencing techniques are particularly well adapted for microarray-based or other solid phase (e.g., microbead) analysis. When the methods are performed on a microarray, target fragments (most often PCR generated fragments) are immobilized on the array, followed by the application of the minisequencing protocol and detection on the microarray. Examples of these approaches are described by Huber et al., 2001, Anal. Biochem. 299: 24–30 and Shapero et al., 2001, Genome Res. 11: 1926–1934.

Functional Testing of PME Nucleotides Useful According to the Invention

PME nucleotide analogs useful according to the invention can be tested for their ability to be recognized and incorporated by a nucleic acid polymerase, and for their ability to act as chain terminators, as follows.

Generally, chain terminator function is tested by setting up a standard primer extension assay and running the assay in the presence and absence of the nucleotide analog. A standard assay will involve, for example, a template nucleic acid molecule in which at least one nucleotide is the complement of the nucleobase carried by the PME nucleotide analog, an oligonucleotide primer that hybridizes to the template, and a nucleic acid polymerase. The primer is annealed to the template in a buffer compatible with the function of the nucleic acid polymerase, followed by the addition of the polymerase and the labeled PME nucleotide analog (plus any conventional nucleotides necessary for primer extension up to a template nucleotide complementary to the PME nucleotide being tested). Reactions are incubated at a temperature compatible with activity of the enzyme, and reaction products are separated on a polyacrylamide gel, followed by detection of incorporated label. Alternatively, following the primer extension reaction, incorporation of labeled PME nucleotide analog can be measured by trichloroacetic acid (TCA) precipitation of the reaction products. Buffers and reaction temperatures are well known in the art for a wide variety of nicleic acid polymerase molecules. If label is incorporated, the PME nucleotide analog serves as a substrate for the polymerase. The fidelity or specificity of incorporation by the polymerase can be further analyzed through the use of specialized templates that, for example, do not have nucleotides complementary to the nucleobase on the analog.

Useful template nucleic acid molecules can exist in a variety of forms, e.g., a single stranded DNA, such as that isolated from an M13 bacteriophage, a plasmid, or a DNA fragment generated by PCR or restriction digest. ). Homopolymers, simple repeats (e.g., AGAGAGAGA . . . ) and templates either devoid of or rich in a given nucleotide are also useful, especially to evaluate the fidelity or specificity of incorporation. Example 1 below describes one set of conditions for evaluation of incorporation and chain termination effects of a PME nucleotide analog.

Chain termination by a PME nucleotide analog according to the invention can be measured by conducting two primer extension reactions containing all four dNTPS (dG, dA, dT, and dC), one reaction with and one reaction without the nucleotide analog. Following the primer extension reaction, reaction products are separated electrophoretically and visualized on the basis of an incorporated label (e.g., attached to the primer, or included as a labeled dNTP). Chain termination is evident if the reaction products made in the presence of the chain terminator are shorter on average than those in its absence, or form a "ladder," where each discretely sized fragment making up the ladder represents a primer extension event terminated after incorporation of the nucleotide analog.

The efficiency of recognition of a given PME nucleotide analog by a given polymerase will influence its usefulness as a chain terminator in nucleic acid sequencing reactions. The effectiveness of a given chain terminator in a reaction catalyzed by a given polymerase enzyme depends upon the $K_d$ of the enzyme-analog interaction. That is, the equilibrium binding constant of the enzyme and the analog determines how much of a given terminator is necessary to bring about chain termination in a reaction also containing non-terminator nucleotides (e.g., deoxynucleoside triphosphates). Generally, the less efficient the interaction, the higher the ratio of chain terminator to non-terminating nucleotide necessary to bring about efficient chain termination.

In order to evaluate the efficiency of recognition of a particular PME nucleotide analog, one can vary the ratio of deoxynucleotide to nucleotide analog in the primer extension reaction. For example, the ratio of nucleotide analog to deoxynucleotide can be varied over a range from from 1:50, to 1:10, to 1:1, to 1:1, to 5:1 and 10:1. If these titration reactions are performed alongside reactions with similar ratios of the corresponding conventional dideoxyNTP, the efficiency of recognition/termination for the polymerase is determined relative to the dideoxyNTP. An example of such a titration is shown in Example 1. While it is preferred that a PME nucleotide analog useful according to the invention will be effective at or below the concentration of the corresponding ddNTP, one skilled in the art can readily adjust the ratios of different chain terminators in order to achieve sequencing results similar to or superior to those achievable using ddNTPs.

Nucleic Acid Polymerases:

Any nucleic acid polymerase that recognizes and incorporates a PME nucleotide analog according to the invention can be used in nucleic acid sequencing methods according to the invention. Incorporation of PME nucleotide analogs by a given polymerase is assessed as described above or in the Examples below. A non-limiting list of nucleic acid polymerases useful or potentially useful according to the invention is provided in Table I. The use of variants of these or other polymerases, e.g., variants modified for reduced discrimination against non-conventional nucleotides, or variants modified so as to recognize or accept a particular modified nucleobase moiety, is also specifically contemplated according to the invention. Reaction conditions specific for a given nucleic acid polymerase will be known to those skilled in the art. Exemplary conditions are provided herein in, for example, in Example 1, below.

TABLE I

DNA POLYMERASES BY FAMILY

FAMILY A DNA POLYMERASES

Bacterial DNA Polymerases a) *E. coli* DNA polymerase I
b) *Streptococcus pneumoniae* DNA polymerase I
c) *Thermus aquaticus* DNA polymerase I
d) *Thermus flavus* DNA polymerase I
e) *Thermotoga maritima* DNA polymerase I
Bacteriophage DNA Polymerases a) T5 DNA polymerase
b) T7 DNA polymerase
c) Spo1 DNA polymerase
d) Spo2 DNA polymerase
Mitochondrial DNA polymerase Yeast Mitochondrial DNA polymerase II

FAMILY B DNA POLYMERASES

Bacterial DNA polymerase

*E. coli* DNA polymerase II
Bacteriophage DNA polymerase a) PRD1 DNA polymerase
b) φ29 DNA polymerase
c) M2 DNA polymerase
d) T4 DNA polymerase
Archaeal DNA polymerase a) *Thermococcus litoralis* DNA polymerase (Vent)
b) *Pyrococcus furiosus* DNA polymerase
c) *Sulfolobus solfataricus* DNA polymerase
d) *Thermococcus gorgonarius* DNA polymerase
e) Thermococcus species TY
f) Pyrococcus species strain KODI
g) *Sulfolobus acidocaidarius*
h) Thermococcus species 9°N-7
i) *Pyrodictium occultum*
j) *Methanococcus voltae*
k) Desulfurococcus strain TOK (D. Tok Pol)
Eukaryotic Cell DNA polymerase (1) DNA polymerase alpha
    a) Human DNA polymerase (alpha)
    b) *S. cerevisiae* DNA polymerase (alpha)
    c) *S. pombe* DNA polymerase I (alpha)
    d) *Drosophila melanogaster* DNA polymerase (alpha)
    e) *Trypanosoma brucei* DNA polymerase (alpha)
(2) DNA polymerase delta
    a) Human DNA polymerase (delta)
    b) Bovine DNA polymerase (delta)
    c) *S. cerevisiae* DNA polymerase III (delta)
    d) *S. pombe* DNA polymerase III (delta)
    e) *Plasmodiun falciparum* DNA polymerase (delta)
(3) DNA polymerase epsilon
    *S. cerevisiae* DNA polymerase II (epsilon)
(4) Other eukaryotic DNA polymerase
    *S. cerevisiae* DNA polymerase Rev3
Viral DNA polymerases a) Herpes Simplex virus type 1 DNA polymerase
b) Equine herpes virus type 1 DNA polymerase
c) Varicella-Zoster virus DNA polymerase
d) Epstein-Barr virus DNA polymerase
e) Herpesvirus saimiri DNA polymerase
f) Human cytomegalovirus DNA polymerase
g) Murine cytomegalovirus DNA polymerase
h) Human herpes virus type 6 DNA polymerase
i) Channel Catfish virus DNA polymerase
j) Chlorella virus DNA polymerase
k) Fowlpox virus DNA polymerase
l) Vaccinia virus DNA polymerase
m) *Choristoneura biennis* DNA polymerase
n) *Autographa california* nuclear polymerase virus (AcMNPV) DNA polymerase

TABLE I-continued

DNA POLYMERASES BY FAMILY o) *Lymantria dispar* nuclear polyhedrosis virus DNA polymerase
p) Adenovirus-2 DNA polymerase
q) Adenovirus-7 DNA polymerase
r) Adenovirus-12 DNA polymerase
Eukaryotic linear DNA plasmid encoded DNA polymerases a) S-1 Maize DNA polymerase
b) kalilo neurospora intermedia DNA polymerase
c) pA12 ascobolus immersus DNA polymerase
d) pCLK1 *Claviceps purpurea* DNA polymerase
e) maranhar neurospora crassa DNA polymerase
f) pEM *Agaricus bitorquis* DNA polymerase
g) pGKL1 *Kluyveromyces lactis* DNA polymerase
h) pGKL2 *Kluyveromyces lactis* DNA polymerase
i) pSKL *Saccharomyces kluyveri* DNA polymerase

Kits Useful According to the Invention

The invention encompasses a kit comprising a PME nucleotide analog useful according to the invention. Kits useful for chain termination reactions can also include a polymerase, or an oligonucleotide primer, or both. The PME nucleotide analog or the primer can be labeled, the label comprising a radiolabel (e.g., $^{32}P$, $^{33}P$, $^{35}S$), a chromophore, a fluorophore, a fluorescence quencher, an enzyme, an enzyme substrate, an affinity tag or an epitope tag recognized by an antibody. In a preferred embodiment, the PME nucleotide is fluorescently labeled.

Kits according to the invention can be tailored towards "traditional" chain terminator sequencing or towards minisequencing approaches. In either instance, a kit can contain more than one (e.g., 2, 3, 4 or more) fluorescently labeled PME nucleotide, wherein each different PME nucleotide bears a spectrally distinguishable fluorophore.

Kits useful according to the invention will also include packaging materials and instructions necessary for use of the kit. Kits can also include one or more standard templates for evaluating the efficiency and/or fidelity of nucleic acid sequencing reactions.

EXAMPLES

Example 1

Assay for Incorporation of Chain Terminators

Reactions (20 µl) consisted of 0.5 pmol fluorescein-labeled primer pFI-20, 1 pmol pBluescript II, 5 U DNA polymerase (JDF-3 P41OL/A485T), all four dNTPs (each at 50 µM) and varying concentrations of only ddATP or PME-App in 20 mM Tris pH 8.8, 10 mM $(NH_4)_2SO_4$, and 2 mM $MgSO_4$. Reactions were incubated in a Perkin-Elmer 9600 for 25 cycles as follows: 95° C. for 30 s, 50° C. for 30 s and 72° C. for 4 min. The reactions were quenched with ice-cold 0.2 M EDTA (final concentration), dried, and the pellets dissolved in a 3:1 formamide: EDTA/blue dextran. Reactions were then analyzed by 6% denaturing PAGE on an ABI 377 sequencer.

Figure 8:
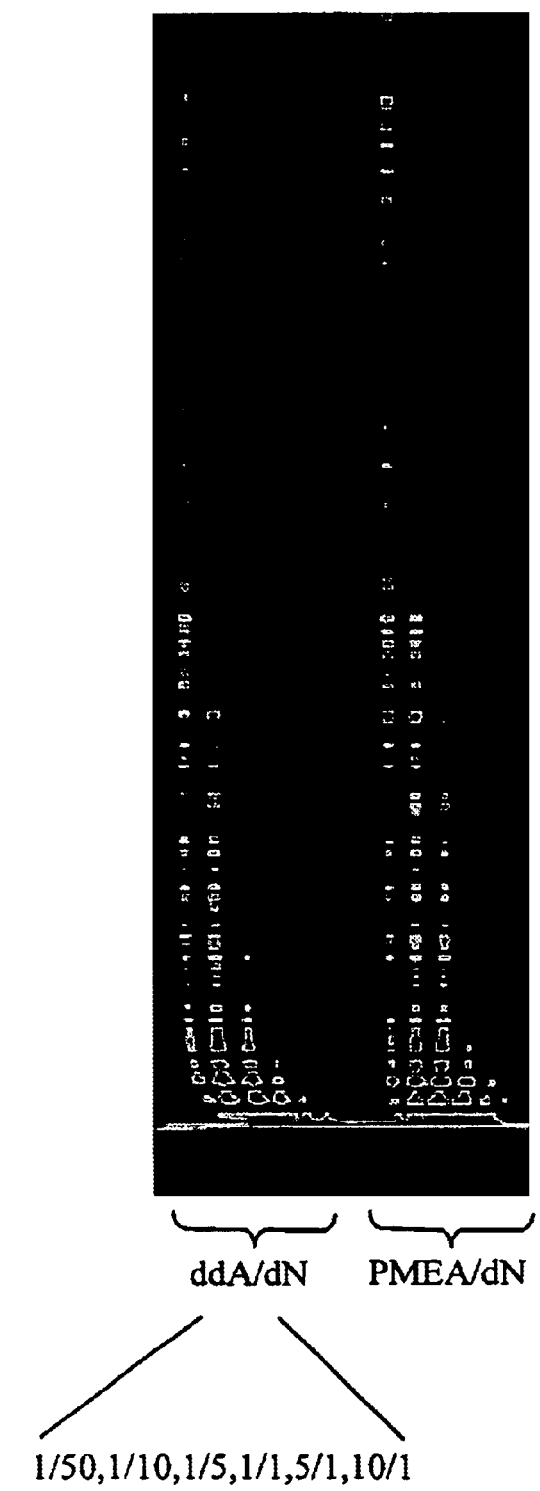
FIG. 8 shows the results of an assay for incorporation of chain terminators. PME nucleotide analog terminator reactions were performed in parallel with ddNTP terminator reactions at the same ratios of terminator to conventional nucleotide.

Results are shown in FIG. 8. Lane 2 of ddATP/dNTP (1/10 ratio) shows a similar pattern (signal strength and length) to the lane 3 of PME-App/dNTP (1/5 ratio), which suggests that ddATP shows 2-fold better inhibition over PME-App. The relative ratio can be determined more exactly by repeating the reactions over a narrower range of ratios.

These conditions are applicable for testing any PME nucleotide analog according to the invention.

---

---

What is claimed is:

1. A detectably labeled phosphonomethoxyethyl nucleotide analog having the general

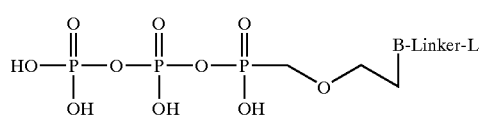

structure wherein L is a detectable label, and L is covalently joined to nucleobase moiety B via a linker.

2. The detectably labeled phosphonomethoxyethyl nucleotide analog of claim 1 wherein said linker is attached to said nucleobase at the N-4 or C-5 position when said nucleobase is a pyrimidine, or at the N-6, C-8 or 7-position, when said nucleobase is a purine or a 7-deazapurine.

3. The phosphonomethoxyethyl nucleotide analog of claim 1 wherein said detectable label is selected from the group consisting of a radionuclide, a chromophore, a fluorophore, a fluorescence quencher, an enzyme, an enzyme substrate, an affinity tag, and an epitope tag recognized by an antibody.

4. The phosphonomethoxyethyl nucleotide analog of claim 1 wherein said detectable label is a fluorophore.

5. The phosphonomethoxyethyl nucleotide analog of claim 4 wherein said fluorophore is selected from the group consisting of Cy5, Cy3, TAMRA, R6G, R110, ROX, JOE, FAM, —$C_{31}H_{29}ClN_2O_6S_2$, $C_{22}H_9F_5O_7S$ and $C_{20}H_{10}F_2O_5$.

6. The phosphonomethoxyethyl nucleotide analog of claim 1 wherein said nucleobase is a purine, a 7-deazapurine, a pyrimidine, or a nucleobase analog thereof capable of forming Watson-Crick base pairs with a nucleobase on an adjacent antiparallel nucleic acid strand.

7. The phosphonomethoxyethyl nucleotide analog of claim 1 wherein the nucleobase is selected from the group consisting of: adenine, cytosine, guanine, thymine, uracil, hypoxanthine, 7-deazapurine, pyrazolo[3,4-d]pyrimidine, imidazo[1,5-a]1,3,5 triazinone, 9-deazapurine, imidazo[4,5-d]pyrazine, thiazolo[4,5-d]pyrimidine, pyrazin-2-one, 1,2,4-triazine, pyridazine; and 1,3,5-triazine.

8. A method of synthesizing a polynucleotide, the method comprising:
    a) annealing an oligonucleotide primer to a template polynucleotide;
    b) contacting the annealed oligonucleotide primer and template of step (a) with a nucleic acid polymerase enzyme with a phosphonomethoxyethyl nucleotide analog of claim 1 diphosphate, under conditions permitting the extension of a nucleic acid primer annealed to a template nucleic acid.

9. The method of claim 8 wherein said contacting results in chain termination.

10. The method of claim 8 wherein said contacting permits the determination of nucleic acid sequence information about said template nucleic acid.

11. The method of claim 8 wherein said phosphonomethoxyethyl nucleotide analog is detectably labeled.

12. The method of claim 11 wherein said detectable label is selected from the group consisting of a radionuclide, a chromophore, a fluorophore, a fluorescence quencher, an enzyme, an enzyme substrate, an affinity tag, and an epitope tag recognized by an antibody.

13. The method of claim 11 wherein said detectable label is linked to the nucleobase moiety of said phosphonomethoxyethyl nucleotide analog.

14. The method of claim 11 wherein said detectable label is a fluorophore.

15. The method of claim 14 wherein said fluorophore is selected from the group consisting of: Cy5, Cy3, TAMRA, R6G, R110, ROX, JOE, FAM, —$C_{31}H_{29}ClN_2O_6S_2$, $C_{22}H_9F_5O_7S$ and $C_{20}H_{10}F_2O_5$.

16. The method of claim 8 wherein the nucleobase of said phosphonomethoxyethyl nucleotide analog is a purine, a 7-deazapurine, a pyrimidine, or a nucleobase analog thereof capable of forming Watson-Crick base pairs with a nucleobase on an adjacent antiparallel nucleic acid strand.

17. The method of claim 8 wherein the nucleobase is selected from the group consisting of adenine, cytosine, guanine, thymine, uracil, hypoxanthine, 7-deazapurine, pyrazolo[3,4-d]pyrimidine, imidazo[1,5-a]1,3,5 triazinone, 9-deazapurine, imidazo[4,5-d]pyrazine, thiazolo[4,5-d]pyrimidine, pyrazin-2-one, 1,2,4-triazine, pyridazine; and 1,3,5triazine.

18. A method of determining sequence information about a template polynucleotide, the method comprising
    a) annealing an oligonucleotide primer to a template polynucleotide,
    b) contacting the annealed primer and template of step (a) with a nucleic acid polymerase enzyme in the presence of a phosphonomethoxyethyl nucleotide analog of claim 1 under conditions sufficient to permit the extension of said primer by said nucleic acid polymerase enzyme, and
    c) detecting the incorporation of said phosphonomethoxyethyl nucleotide analog onto said primer, wherein said incorporation determines sequence information about said template polynucleotide.

19. The method of claim 18 wherein said method is performed on a solid support.

20. The method of claim 18 wherein said phosphonomethoxyethyl nucleotide analog is detectably labeled.

21. The method of claim 20 wherein said phosphonomethoxyethyl nucleotide analog is fluorescently labeled.

22. The method of claim 21 wherein, following completion of steps (a)–(c), steps (b) and (c) are repeated at least once more in the presence of a differentially labeled phosphonomethoxyethyl nucleotide analog wherein the nucleobase of said nucleotide analog is different from that used in the prior execution of steps (a)–(c).

23. A kit comprising a phosphonomethoxyethyl nucleotide analog of claim 1.

24. The kit of claim 23 wherein said phosphonomethoxyethyl nucleotide analog is a phosphonomethoxyethyl diphosphate nucleotide analog.

25. A kit comprising a phosphonomethoxyethyl nucleotide analog and a nucleic acid polymerase.

26. A kit comprising a phosphonomethoxyethyl nucleotide analog of claim 1 and an oligonucleotide primer.

27. The kit of claim 25 further comprising an oligonucleotide primer.

28. The kit of claim 23 wherein said phosphonomethoxyethyl nucleotide analog is detectably labeled.

29. The kit of claim 28 wherein said detectable label is selected from the group consisting of a radionuclide, a chromophore, a fluorophore, a fluorescence quencher, an enzyme, an enzyme substrate, an affinity tag, and an epitope tag recognized by an antibody.

30. The kit of claim 28 wherein said detectable label comprises is a fluorophore.

31. The kit of claim 30 wherein said fluorophore is selected from the group consisting of Cy5, Cy3, TAMRA, R6G, R110, ROX, JOE, FAM, —$C_{31}H_{29}ClN_2O_6S_2$, $C_{22}H_9F_5O_7S$ and $C_{20}H_{10}F_2O_5$.

32. The kit of claim 23 wherein the nucleobase of said nucleoside analog is a purine, a 7-deazapurine, a pyrimidine, or a nucleobase analog thereof capable of forming Watson-Crick base pairs with a nucleobase on an adjacent antiparallel nucleic acid strand.

33. The kit of claim 32 wherein the nucleobase is selected from the group consisting of: adenine, cytosine, guanine, thymine, uracil, hypoxanthine, 7-deazapurine, pyrazolo[3,4-d]pyrimidine, imidazo[1,5-a]1,3,5 triazinones, 9-deazapurines, imidazo[4,5-d]pyrazines, thiazolo[4,5-d]pyrimidines, pyrazin-2-ones, 1,2,4-triazine, pyridazine; and 1,3,5-triazine.

34. The kit of claim 28 wherein said detectable label is a radionuclide.

35. The kit of claim 34 wherein said detectable label consists of a radionuclide covalently linked to the phosphorus atom of the phosphonomethoxy group.

36. The kit of claim 35 wherein said radionuclide is $^{35}$S.

37. The kit of claim 34 wherein the phosphorus in the phosphonomethoxy moiety consists of $^{32}$P or $^{33}$P.

* * * * *